United States Patent
Van Der Laan et al.

[11] Patent Number: 6,033,823
[45] Date of Patent: Mar. 7, 2000

[54] MUTATED PENICILLIN G ACYLASE GENES

[76] Inventors: Jan M. Van Der Laan, Leursebaan 364, Breda 4839 AP; Adriana M. Riemens, Knuttelstraat 36, Delft 2613 XX; Wilhelmus J. Quax, J. van Galenlaan 8, Voorschoten 2253 VB, all of Netherlands

[*] Notice: This patent is subject to a terminal disclaimer.

[21] Appl. No.: 09/285,957

[22] Filed: Apr. 5, 1999

Related U.S. Application Data

[63] Continuation of application No. 08/793,229, filed as application No. PCT/EP95/03249, Aug. 14, 1995, Pat. No. 5,891,703.

[30] Foreign Application Priority Data

Aug. 12, 1994 [EP] European Pat. Off. ............... 94202314

[51] Int. Cl.[7] .............................. C12N 9/84; C12N 15/11; C12N 15/55; C12N 15/70
[52] U.S. Cl. .............................. 430/230; 435/44; 435/45; 435/69.1; 435/252.3; 435/252.33; 435/320.1; 435/471; 536/23.2; 536/23.7; 935/10; 935/14; 935/29; 935/73
[58] Field of Search ............................... 435/230, 44, 45, 435/69.1, 252.3, 252.33, 320.1, 471; 536/23.2, 23.7

[56] References Cited

U.S. PATENT DOCUMENTS

| | | | |
|---|---|---|---|
| 4,774,179 | 9/1988 | Ichikawa et al. | 435/51 |
| 5,168,048 | 12/1992 | Quax | 435/230 |
| 5,192,678 | 3/1993 | Iwami et al. | 435/228 |
| 5,320,948 | 6/1994 | Iwami et al. | 435/47 |
| 5,336,613 | 8/1994 | Niwa et al. | 435/228 |
| 5,457,032 | 10/1995 | Quax et al. | |
| 5,516,679 | 5/1996 | Chiang et al. | 435/230 |
| 5,695,978 | 12/1997 | Quax | 435/230 |
| 5,891,703 | 4/1999 | Van Der Laan et al. | 435/230 |
| 5,935,831 | 8/1999 | Quax et al. | 435/172.3 |

FOREIGN PATENT DOCUMENTS

| | | |
|---|---|---|
| 0283218 | 9/1988 | European Pat. Off. . |
| 0322032 | 6/1989 | European Pat. Off. . |
| 0 453 048 | 10/1991 | European Pat. Off. . |
| 0558241A2 | 9/1993 | European Pat. Off. . |
| WO 95/12680 | 5/1995 | WIPO . |
| WO 98/20120 | 5/1998 | WIPO . |

OTHER PUBLICATIONS

Fei, J., et al., Shiyan Shengwu Xuebao (Acta Biologiae Experimentalis Sinica), vol. 25, "Studies on the function of Ser579 and Arg580 in beta–subunit of penicillin G acylase with the method of site–specific mutagenesis", pp. 289–293, 1992.

Brannigan, J. et al., Perspectives in Protein Engineering [Geisow, M. J., et al., Eds.; Mayflower Worldwide, Pub.], "Altered specificity mutants of penicillin acylase", pp. 124–125, 1995.

Duggleby, H. J., et al., Nature, vol. 373, "Penicillin acylase has a single–amino–acid catalytic center", pp. 264–268, 1995.

Barbero et al., *Gene*, (1986) 49: 69–80.

Daumy, *J. Bacteriol*, (1985) 163: 1279–1281.

Forney et al., *Applied & Environmental Microbiology*, (1989) 55: 2550–2560.

Joris et al., *Biochem. J.*, 250, 313–324 (1988).

Martin et al., *Biochim. Biophys. Acta*, 1037 (2), 133–139 (1990).

Matsuda et al., *J. Bacteriol.*, (1987) 169: 5815–5820.

Matsuda et al., *J. Bacteriol.*, (1987) 169: 5821–5826.

Norrander et al., *Gene*, (1983) 26: 101–106.

Prieto et al., *Appl. Microbiol. Biotechnol.*, 33 (5), 553–559 (1990).

Schumacher et al., *Nucleic Acids Research*, (1986) 14: 5713–5727.

Stanssens et al., *Nucleic Acids Research*, (1989) 12: 4441–4454.

Williams et al., *J. Cell. Biochem.*, 9(b) (Suppl.), 99 (1985), Abstract No. 0656.

*Primary Examiner*—Ponnathapu A. Chutamurthy
*Assistant Examiner*—William W. Moore
*Attorney, Agent, or Firm*—McDonnell Boehnen Hulbert & Berghoff

[57] ABSTRACT

New mutant β-lactam Penicillin G acylases are provided, exhibiting altered substrate specificities. These Penicillin G acylases are obtained by expression of a gene encoding said Penicillin G acylase and having an amino acid sequence which differs at least in one amino acid from the wild-type Penicillin G acylase.

13 Claims, 13 Drawing Sheets

Fig. 2a

```
afae_A  126 QPEPLTDFDVVMIWVGSMANRFSDTNLEVTALAMRQSLEKQHGPERGRAL 166
ecol_A  125 TKRWEPA***F*T***STS*IDN**LLTA*KDKY*VSQ*M*V
kcit_A  125 KKHWEPA***F*T***STS*IDN**LLTAVKDKY*NDE*M*V 165
avis_A  125 L*QKW*STRVYMV*TYLWII*R*LKNAEILAK**HEY*T*VS*KM 164
pret_A  146 L*SQW*S*A*M*T*****M*S*IDN**LLTA*KDKY*EQL*VEF 186 afae_A  176 FDELLWINDTTAPTTVPAPAAEHKPQA 0
ecol_A  175 *NQ*K*LVNPS***IAVQESNYPLKFNQQNSQTA 205
kcit_A  175 *NQ*K*LVNPS***IA*RESSYPLKFDLQNTQTA 205
avis_A  174 **D*V*K*PSSIVSEGKPKRESSSQSLQKL 204
pret_A  196 *NQIN*L*NPN***ISSEEFTYSDSQKTKNISQLNQISDYRLTAPMFER 236 pret_A  246 TAKDTTGKVLALSSQENNALIAKQYEQSGANGLAGYPTT 276
```

Fig. 2b

```
afae_B    1 SNLWSTRPERVQEGSTVLINGPQFGWYNPAYTYGIGLHGAGFDVVGNTPF
ecol_B    1 * * * * * * * * * * * * * * * * * * * * * * * * * * * * * * * * * * * * * * * * * * * * * * * * *
kcit_B    1 * * M * VIGKSKA * DAKAIMV * * * * * A * * * * * * * Y * * T * * *
avis_B    1 * * M * VIGKNKA * DAKAIMV * * * * * A * * * * * * * Y * * T * * *
kcit_B    1 * * AAIVGS * KSAT * NAL * FS * * * * V * GFL * EV * * * AP * * * ME * SGFI
pret_B    1 * * V * LVGKTKASGAKAI * * L * * * * * * F * * * * * * * * * NI * * * * * afae_B   51 AYPIVLFGTNSEIAWGATAGPQDVVDIYQEKLNPSRADQYWFNNAWRTME
ecol_B   51 * * * GLG * * * H * GV * * S * * FG * D * * * FA * R * SAEKPGY * LH * GK * VK * L
kcit_B   51 * * * GLV * * * H * GT * * S * * FG * D * * * FA * * * SAEKPGY * QH * GE * VK * L
avis_B   51 G * * FIM * * A * NHF * LS * * * * * YGN * T * * * FE * * * * TKNSS * LYKGK * D * *
pret_B   51 * * * AI * * H * GHVS * * * S * * FG * G * * * FA * QVS * EDPNS * LHQGQ * KK * L afae_B  101 QRKERIQVRGQADREMTIW   119 RTVHGPVMQFDYDQGAAYSKKRSWDGY
ecol_B  101 S * * E * T * KNGQAETF * V *   119 * * * NIL * T * QTTQT * A * S * A * * K
kcit_B  101 S * * * T * * A * KDGQPETF * V *   119 * * * N * IKT * TRTQT * A * A * A * * K
avis_B  101 K * * * SFT * * DNGEKK * VEKIYY   121 * * LD * * ISR * ETNKV * * YV * FR * T
pret_B  101 S * Q * TLN * K * EQPITFE * Y   119 * * * N * VKR * KTTHT * * A * A * * K
```

Fig. 2c

```
afae_B  146 EVQSLLAWLNVAKARNWTEFLDQASKMAISINWYYADKHGNIGYVSPAF
ecol_B  146 *A*****K**Q*WTQ****A*Q********VN******HTGA
kcit_B  146 *AA****K**P*WTQ****A*Q********VN******HTGA
avis_B  151 *AA****LK*ENA****EYTM*L******KA*YHVGR
pret_B  146 *LTM*VKQGQ*Q*QQWQNQ*LT*******DHTGH 196
afae_B  196 LPQRPADQDIRVPAKGDGSMEWLGIKSFDAIPKAYNPPQGYLVNNNKPA
ecol_B  206 ***D*QSGH**P*L**VP*T******KWD**K*LLP*L***QS*IA******S*Q
kcit_B  206 ***D*QPGH**P*LVP***KWDK*LL**V*QS*IA******S*Q
avis_B  211 ***V*NNKI*E**TP*T*EYFIP*KEN*HVI*KNV******S
pret_B  206 ***D*QINH*P*L**VS*T*EWDK***QP*ANN*****KS*IA******S*

246                                                       284
afae_B  246 PDKTNTDTYYWTYG     DRMNELVSQYQQKDLFSVQEIWEFNQKASYSDVN
ecol_B  256 K**YPAS*LFAFLW*GA***VT*IDRLLE****PRLTADQA*DVIRQT*RQ*L*
kcit_B  255 K**YPAS*LFAFLW*GA***VT******PR*TADQA*DVIRQT*LR*LL
avis_B  261 KEWV*GEYS*YWGEDNRVQQYINGGMEARGKVTLED*N*I*YT**FAQLR
pret_B  256 KNYPAS*LFAFLW*SA**VK*IDNRIEAY*KLTADDM*AIL*QT*RV*L*
```

Fig. 2d

```
afae_B  294 WRYFRPHLEKLAQQLPADDSSKAALTMLLAWDGMEQDQ            GGQNAGPARV
                                              324         332
ecol_B  296 LLL**T*QAATSG*TQS*PRRQLVET*TR***INLLNDD*KTWQQ*GSA
               304           314          326                336
kcit_B  294 *LLLAKDATAN*AEN*PRRQLVET*AS***ENLVNDD*KTYQQ*GSA
               304           314          324                334
avis_B  301 ANLKL*IDVLDKNKSTNGNYTY*IEK*EEWNNLKEDENKDGYYDAGIA
               311          321           331              341
pret_B  296 HLT*F*TQAT*G***SN*N*VKLVSQQ*IN*LSSD*KHYIH*GSA
               306          316         326                336 afae_B  342 LFKTWLEEMYKQVLMPVVPESHRAMYSQTGFATQQGPNPGSINLSMGTKV
               352          362          372          382
ecol_B  346 ILNV**TS*L*RTVVAA*MPFDKWAS*YE*T*DGPT*LLIVA**I
               356          366          376
kcit_B  344 ILNA**TS*L*RTVAAAPFGKW**AS*YE*T*DGPT*LLIVA**I
               354          364          374
avis_B  351 A**FDEWWNNLHDK*FMDELGDFYGITKEITDHRYGASLAYKNISKES*NY
               361          371          381           391
pret_B  346 YLDIKL*AT*GQT**APFDKW*LAS*YE*T*EGPT*LIT*A**L
               356          366          376          386 afae_B  392 LLRALVLEAHPDDPKRVNVFGERSSQEIMHTALQNAQARLSQEQGAQMARW
               402          412          422          432
ecol_B  396 *YE**VQGDKS*I**QA*DLAGKPQVVLA*EDTWETKRYNNVSN*
                406          416          426           436
kcit_B  394 *YE**QGDKS*I**QA*DL*GKPEVILA**DD*WQT**KRY*NDVTG*
                404          414          424           434
avis_B  401 KWVKW*NVDQE         KIIME*TN*VLAKLQSEKGLKAEKWRMPI
               411                425                  435
pret_B  396 *YES*LEDKS*ISQSIDL*SGQPQNDVIRKT*NTTYQKMIEKY*DNP**N*
                406          416          426          436
```

Fig. 2e

```
afae_B  442 TMPTSVHRFSDKNFTGTPQTMPGNTFAFTGYQNRGTENNRVVFDAKG
             446              452         462         472         482
ecol_B  446 KT*AMALT*RAN*****F*V**AAAEE*RHQAE*******DMI**SPTTSDR
             444              454         464         474         486
kcit_B  440 KT*AMALT*RAN*****F*VAAAKEARHQAE***DMISPTSGNR
             446              456         465         475         484
avis_B      KTMTFGEKSLIGIPHGY GSMTPIIEM*****S***HYIEMTP**
             446              456         466         476         486
pret_B      QT*ATALT*REN*****F*I***AL*QEN*HQNE*H**DLIT       EE afae_B  488 VEFCDAMPPGQSGFTDRNGVRSPHYEDQLKLYENFECKTMDVTHADIRR
             498              508         518         528
ecol_B  496 P*LAW*VVA*****IAPD*TVDK***M****GR*SLWL*KQ*VEA
             504              514         524         536
kcit_B  494 P*LAW*VVA*****IAPD*KADK***D***M***S*GR*SLWL*PQ*VDE
             491              501         511         521         534
avis_B  492 PSGFNIT*****I***VKKD*TI*D***D****VMFAEWKF*PYLFNKK *
             502              512         522         532
pret_B      G*SAW*VVA*****ISPQ*KP****QS**QQ*GK*PLWLNSE*VAP afae_B  538 NAQSSTMLLIQPQP                                    0
             548
ecol_B  546 HKE*QEV*HV*R                                      0
             556
kcit_B  544 HKE*QEV*QV*R                                      0
             554
avis_B  542 YIE*TET*I*ER                                      0
             552
pret_B                                                         0
```

Fig. 2f

MUTATED PENICILLIN G ACYLASE GENES

REFERENCE TO RELATED APPLICATION

This application is a continuation of U.S. Ser. No. 08/793,229, filed Apr. 23, 1997 now issued as U.S. Pat. No. 5,891,703, which itself is a national phase application of PCT International Application No. 96/05318 filed Aug. 14, 1995 as PCT/EP95/03249. Additionally, this application claims the priority of European Patent Application No. EP 942023144 filed in the Netherlands on Aug. 12, 1994.

FIELD OF THE INVENTION

The present invention relates to mutations of prokaryotic Penicillin G acylase or its preenzyme or preproenzyme, resulting in altered properties of the mutant penicillin G acylase.

BACKGROUND OF THE INVENTION

The basic antibiotics of the β-lactam type are principally obtained by fermentation. Fungi of the genus Penicillium and Cephalosporium (Acremonium) are used for the production of raw material for β-lactam antibiotics as penicillin G, penicillin V and cephalosporin C. These fermentation products, also referred to as PenG, PenV and CefC, respectively, are the starting materials for nearly all currently marketed penicillins and cephalosporins. In general the acyl group at the 6-amino of the penicillin nucleus or at the 7-amino position of the cephalosporin nucleus is referred to as 'side chain', the corresponding acid as 'side chain acid'. The side chains of PenG, PenV and CefC are phenylacetyl, phenoxy-acetyl and aminoadipyl, respectively. The side chains are removed by cleavage of an amide linkage (deacylation), resulting in 6-aminopenicillanic acid (6-APA) in case of the penicillin molecules and 7-aminocephalosporanic acid (7-ACA) in case of the cephalosporin molecule. In this respect also phenylacetyl-7-aminodesacetoxycepha-losporanic acid (CefG) should be mentioned as a precursor of 7-ADCA, although CefG is not a fermentation product. CefG is usually produced chemically from Penicillin G.

In order to obtain β-lactam compounds with an altered activity spectrum, an increased resistance against β-lactanases or improved clinical performance of β-lactam compounds, 6-APA, 7-ACA and 7-ADCA are used as starting points for synthetic manipulation to produce the various penicillins and cephalosporins of choice. At present these semisynthetic penicillins and cephalosporins form by far the most important market of β-lactam antibiotics.

The production of semisynthetic β-lactam products requires the deacylation of the penicillins and cephalosporins produced from fermentation. Although rather efficient chemical routes are available for the deacylation (J. Verweij & E. de Vroom, Recl. Trav. Chim. Pays-Bas 112 (1993) 66–81), nowadays the enzymatic route is preferred in view of the high energy and solvents cost together with some environmental problems associated with the chemical route (Dunnill, P., Immobilised Cell and Enzyme Technology. Philos, Trans. R. Soc. London B290 (1980) 409–420). The enzymes which may accomplish the deacylation of β-lactam compounds are classified as hydrolases based on the chemical reaction they catalyse. However, those hydrolases which are particularly useful in the deacylation is of β-lactam compounds are usually referred to in the art as 'acylases' or 'amidases'. These denominations as used in this specification have the same meaning. In connection with β-lactam antibiotics these acylases usually are further specified as 'β-lactam acylases' as not all amidases accept a β-lactam nucleus as an acceptor/donor moiety for the acyl group. According to the literature several types of β-lactam acylases may be envisaged, based on their substrate specificity and molecular structure (B. S. Deshpande et al., World J. Microbiology & Biotechnology 10 (1994) 129–138).

Acylase, Nomenclature & Classification

Classification according to Specificity.

The substrate specificity of the acylase is determined by a side chain binding pocket at the enzyme which recognizes the side chain moiety of β-lactam molecules. In general, the acylases are not very specific for the moiety adjacent to the nitrogen atom of the amide group (this might be a cephem group, a penem group, an amino acid, sugars, etc. (J. G. Shewale et al., Process Biochemistry International, Jun. 1990, 97–103). In case of the Penicillin G acylases (Benzylpenicillin amidohydrolase, also named Penicillin amidase; EC 3.5.1.11) this acyl moiety must be very hydrophobic and is preferably phenylacetyl or (short) alkyl. Penicillin G acylase is used commercially to hydrolyse PenG or CefG to phenylacetic-acid and 6-APA or 7-ADCA, respectively the most important intermediates for the industrial production of semi-synthetic penicillins and cephalosporins. Beside these major applications other have been reported for these enzymes such as blocking/deblocking of sensitive groups in organic synthesis and peptide chemistry, stereospecific conversions, optical resolution of phenylglycine, deesterification of carbinols, acylation of mono-bactams etc. In the various applications the enzyme may be used C. either in its native state or as immobilised preparation. Microbial whole cells containing the enzyme activity have also been used either as cell suspension or as immobilised cell preparation.

Examples of substrates which are not hydrolyzed by Penicillin G acylases are those with charged acyl moieties such as dicarboxylic acids: succinyl, glutaryl, adipyl and also amino-adipyl, the side-chain of CefC.

Penicillin V acylases are highly specific for phenoxyacetyl, while ampicillin acylase prefers D-phenylglycine as a side chain. Glutaryl-acylases deacylate glutaryl-7-ACA, which is prepared from CefC after enzymatic deamidation of the side chain with D-amino acid oxidase followed by chemical decarboxylation of the formed ketoadipyl derivative with peroxide, which is produced in the first step. Moreover some of these acylases have been reported to be capable of hydrolyzing cephalosporins (including the desacetoxy-derivative) with succinyl, glutaryl and adipyl as an acyl moiety and even in one case CefC to a very limited degree (for a review see EP-A-322032, Merck). So far these acylases have only been found in Pseudomonas species, and in certain strains of Bacillus megaterium and Arthrobacter viscosus.

Classification based on structural properties of the enzymes.

Apart from their specificities acylases may also be classified based on molecular aspects (V. K. sudhakaran et al., Process Biochemistry 27 (1992) 131–143):

Type-I acylases are specific for Penicillin V. These enzymes are composed of four identical subunits, each having a molecular weight of 35 kDa.

Type-II acylases all share a common molecular structure: these enzymes are heterodimers composed of a small subunit (α; 16–26 kDa) and a large subunit (β; 54–66 kDa). With respect to the substrate specificity, Type-II acylases may be further divided into two groups:

Type-IIA acylases comprise the Penicillin G acylases;

Type-IIB acylases comprise the Glutaryl acylases.

Type III acylases are the Ampicillin acylases which have been reported to be dimers consisting of two identical subunits with a molecular weight of 72 kDa.

Benefits of Protein Encineerina with Respect to Screening/Chemical Modification

Enzymes with improved properties can be developed or found in several ways, for example, by classical screening methods, by chemical modification of existing proteins, or by using modern genetic and protein-engineering techniques.

Screening for organisms or microorganisms that display the desired enzymatic activity, can be performed, for example, by isolating and purifying the enzyme from a microorganism or from a culture supernatant of such microorganisms, determining its biochemical properties and checking whether these biochemical properties meet the demands for application. The present collection of acylases results from intensive screening programs. β-lactam acylase activity has been found in many microorganisms such as fungi, yeast, actinomycetes and bacteria.

If the identified enzyme cannot be obtained from its natural producing organism, recombinant-DNA techniques may be used to isolate the gene encoding the enzyme, express the gene in another organism, isolate and purify the expressed enzyme and test whether it is suitable for the intended application.

Modification of existing enzymes can be achieved inter alia by chemical modification methods. In general, these methods are too unspecific in that they modify all accessible residues with common side chains or they are dependent on the presence of suitable amino acids to be modified, and often they are unable to modify amino acids difficult to reach, unless the enzyme molecule is unfolded. In addition chemical modification require Additional processing steps and chemicals to prepare the enzyme. Enzyme modification through mutagenesis of the encoding gene does not suffer from the problems mentioned above, and therefore is thought to be superior.

Moreover the choice for an acylase, subsequent construction and selection of high-yielding penicillin acylase-producing strains and the development of an industrial process for isolation and immobilisation, is a laborious process. In general for production and subsequent formulation of the mutants the wild type protocols can be followed. Therefore, once such a process has been developed successfully for a certain acylase it is very attractive to broaden the application of the acylase of choice instead of continuing the screening for enzymes from other sources. Therefore enzyme modification through mutagenesis of the encoding wild type gene is thought to be superior to screening especially when small adaptation of the properties of the enzyme are required. Desired properties may include altered specificity, altered specific activity for a certain substrate, altered pH dependence or altered stability. Mutagenesis can be achieved either by random mutagenesis or by site-directed mutagenesis.

Random mutagenesis, by treating whole microorganisms with chemical mutagens or with mutagenizing radiation, may of course result in modified enzymes, but then strong selection protocols are necessary to search for mutants having the desired properties. Higher probability of isolating desired mutant enzymes by random mutagenesis can be achieved by cloning the encoding enzyme, mutagenizing it in vitro or in vivo and expressing the encoded enzyme by recloning of the mutated gene in a suitable host cell. Also in this case suitable biological selection protocols must be available in order to select the desired mutant enzymes.

Site-directed mutagenesis (SDM) is the most specific way of obtaining modified enzymes, enabling specific substitution of one or more amino acids by any other desired amino acid.

The conversion of β-lactam intermediates to the desired semi-synthetic antibiotics may be performed chemically and enzymatically. If a suitable enzyme is available the enzymatic route is preferred because:

reactions can be performed stereospecifically;

reactants do not require side chain protection such as silylation;

less need for organic solvents, i.e. an organic solvent such as methylene chloride can be omitted which reduces environmental problems;

compared to the chemical route usually less steps are required;

neither extreme temperatures nor pressures required;

usually lower content of byproducts.

Synthetic manipulation to produce the various penicillins and cephalosporins of choice basically starts from 6-APA, 7-ACA and 7-ADCA, respectively.

The enzymatic conversion takes advantage of the fact that any enzymatic reaction is reversible, if the correct conditions are applied. The importance of such applications has been highlighted in previous reviews. The literature gives several examples of the application of penicillin acylases in biosynthetic routes (J. G. Shewale et Al., Process Biochemistry International, June 1990, 97–103). Acyl derivatives of 6-APA, 7-ADCA, 7-ACA, 3-amino-4-α-methyl monobactamic acid and peptides have been prepared with side-chain moieties of varying structure. Besides 6-APA and 7-ADCA, penicillin acylase is used in the formation of antibiotic intermediates such as 6-amino-2,2-dimethyl-3-(tetrazol-5-yl) penam, methyl-6-aminopenicillate, 3-methyl-7-amino-3-cephem-4-carboxylic acid and 3-amino nocardic acid. The hydrolytic raction is catalysed at alkaline pH (7.5–8.5) while at acidic or neutral pH (4.0–7.0) it promotes acylation reactions.

Various factors affect the performance of an acylase in bioconversion processes:

reaction medium: pH, ionic strength, temperature, organic solvents, etc.;

enzyme stability with respect to process conditions;

reactant stability;

catalytic activity of the enzyme.

Except reactant stability which is not an enzyme property, the other factors may be a target for enzyme modification via protein engineering.

Various of these factors have been explored in order to make biosynthesis processes economically viable. Methylesters which are superior acyl donors as compared to free acids of side chain acids have been used in the reaction. The equilibrium of the reaction has been shifted in favour of acylation by changing the water activity around the enzyme molecule with certain solvents. E.g. polyethyleneglycol, methanol, ethanol, propanol, butanol, and acetone are used in enhancing the yield of penicillin G, penicillin V and ampicillin.

Acylation reactions especially with 6-APA, 7-ADCA and 7-ACA generate antibiotics which are clinically important. However, the reaction needs to be monitored under strict kinetically controlled parameters. Although in some articles it was speculated that protein-engineering tools might be explored to obtain tailored enzyme molecules giving semi-synthetic penicillins and cephalopsorins at a yield competing with existing chemical processes, there was no teaching whatsoever neither how this should be carried out, nor which enzymes should be engineered, or which amino acid residues should be substituted, nor any relation between the kind of substitution and the desired substrate.

The synthetic potential of a given penicillin acylase is limited due to the specificity of the enzyme. Therefore, there is a substantial interest in developing enzymes which are highly efficient in deacylation/acylation reactions to producedesired chemical entities. Of particular interest are the enzymatic deacylation of β-lactams (especially PenG, PenV, CefC, and derivatives thereof) to 6-APA and 7-ACA and derivatives, and the acylation of the latter compounds to produce semi-synthetic pencillins and cephalosporins of interest. In addition increased activity on more polar side chains or charged side chains such as succinyl, glutaryl or adipyl is desired. In particular, it is of major importance to dispose of an efficient enzyme which is capable of catalyzing the conversion of CefC (and derivatives) to 7-ACA (and derivatives).

Theoretical Aspects of the Application of Enzymes in Synthesis

Penicillin G acylases are hydrolases which catalyse the deacylation of various β-lactam compounds. Moreover as enzymes catalyse reactions in both directions, these acylases may also be used as a transferase to catalyse the synthesis of condensation products such as β-lactam antibiotics, peptides, oligosaccharides or glycerides. Enzyme catalysed synthesis may be carried out either as an equilibrium controlled or as a kinetically controlled reaction.

In an equilibrium controlled process the enzyme only accelerates the rate at which the thermodynamic equilibrium is established. The kinetic properties of the enzyme do not influence the equilibrium concentrations. However, the thermodynamic equilibrium is dependent on reaction conditions such as pH, temperature, ionic strength, or solvent composition. Often the conditions which favour the shift of the thermodynamic equilibrium in such a way that an optimal yield of the desired product is obtained are usually not optimal for the performance of the enzyme. In such cases enzyme engineering may be desired to adapt the enzymes to conditions which are closer to the thermodynamic optimum of the reaction. In this aspect properties such as stability, temperature optimum and pH optimum may be useful targets.

In kinetically controlled reactions conditions are chosen in such way that a considerable accumulation occurs of the desired product during the reaction under non-equilibrium conditions. In this case besides the already mentioned parameters also the kinetic properties of the enzyme are an important factor in obtaining yields which can compete favourably with existing chemical processes.

The kinetics of Penicillin G acylase. are consistent with catalysis proceeding via an acyl-enzyme intermediate. This intermediate plays a key role in the enzyme mechanism as is depicted in FIG. 1. In this scheme the acylase acts as a hydrolase where the acyl group is transferred to water, or as a transferase where the acyl transfer from an activated substrate to a nucleophile is catalyzed. The chemical entities are represented by general formulas. The nature of the chemical entities X and Y in compound X—CO—NH—Y which are accepted as a substrate by a particular acylase is determined by the specificity of that acylase. X represents the side chain, while Y represents the acyl acceptor group. For instance, for the deacylation of PenG, X—CO— represents the phenyl-acetyl side chain and —NH—Y represents 6-aminopenicillic acid. Given a certain enzymatic mechanism the specificity is determined by the is architecture and the amino acid composition of the binding sites for X and Y.

In the first step of the mechanism, the substrate binds to the enzyme to form the non-covalent Michaelis-Menten complex. In the subsequent step, the covalent intermediate is formed between the enzyme and the acyl moiety of the substrate (E—CO—X). Formation of the acyl-enzyme may occur through cleavage of an amide bond (amide hydrolysis of X—CO—NH—Y) or an ester bond (ester hydrolysis X—CO—O—R) and at low pH it may also be formed directly from X—COOH. The nucleophile YNH binds to the acyl-enzyme before deacylation. Under conditions which favour the deacylation (the enzyme acts as a deacylase or amidase) a water molecule will hydrolyse the acyl enzyme thereby liberating the second product X—COOH and regenerating the enzyme for a new catalytic cycle. Under conditions which favour formation of compound X—CO—NH—Y, the nucleophile Y—NH reacts with the acyl enzyme instead of water (aminolysis). For PenG the mechanism above was confirmed by the observations that phenylacetic acid acts as a competitive inhibitor and 6-APA as a non-competitive one.

In general the formation of the acyl-enzyme from amides ($v_1$) is slow compared to the hydrolysis of the acyl enzym ($v_3$). However, when the appropriate ester derivatives of the side chain are used (X—CO—O—R) or just the amide (X—CO—NH2) then the formation of the acyl-enzyme ($v_2$) is relatively fast in comparison with hydrolysis ($v_3$). The consequence is that the acyl enzyme intermediate will accumulate. In the presence of suitable compounds with a free primary amino group (general representation Y—NH2) such as, for example, 6-APA, 7-ACA, 7-ADCA which are bound by the acylase, an amide bond may be formed giving X—CO—N—Y ($v_{-1}$, aminolysis).

With respect to the preference for chemical entities X and Y substitution of residues in the binding sites for X and Y at the enzyme alter this preference. Changes in substrate specificity include all combinations of increase and decrease of $V_{sax}$ and $K_s$. In some cases a more specific enzyme is required, e.g. with mixtures of enantiomers it may be useful when the enzyme is selective for only one of the enantiomers. In other cases, e.g. the conversion of rather pure compounds, a higher conversion rate might be preferred at the cost of selectivety. At high substrate concentrations a higher $V_{sax}$ is preferred while Km is less important.

Acylases used for substrate activation and kinetically controlled synthesis may be altered in such a way that their catalytic ability to hydrolyse compounds ($V_3$=transfer acyl group to water) has been suppressed with respect to acyl transfer to a non-aguous acceptor nucleophile ($v_{-1}$): ratio $V_{-1}/V_3$ increased relative to wild type.

The ratio of transferase to hydrolase activity is the enzyme property that influences yield in kinetically controlled synthesis of condensation products. The ratio of the apparent second order rate constants for the acyl transfer to YNH or H20 can be determined from the initial rates of formation of X—CO—NH—Y and X—COOH from the acyl-enzyme.

Transferase activity may be improved by improving the affinity of the nucleophile for the enzyme-acyl complex with respect to water. As the transfer of the acyl group ($v_{-1}$) is proportional to amount of nucleophile bound to the acyl-enzyme an increased affinity for the enzyme-acyl complex will improve the yield of the condensation product with respect to hydrolysis.

In addition a higher yield in an enzyme catalysed biosynthesis may be obtained by reducing the hydrolysis of the desired products ($v_1v_3$). Variants for which the hydrolysis of amide bonds relative to ester bonds has been decreased are still able to form the acyl enzym from ester substrates ($v_2$) but have relatively weak hydrolysis activity for the product amide bond (increased ratio $v_1/V_2$ with respect to wild type).

Relevant Literature

Several genes encoding Type-IIA Penicillin G acylases have been sequenced, viz. the genes from E. coli (G. Schumacher et al., Nucleic Acids Research 14 (1986) 5713–5727), Kluyvera citrophila (J. L. Barbero et al., Gene 49 (1986) 69–80), Alcaligenes faecalis (U.S. Pat. No. 5,168,048, Gist-brocades), Providencia rettgeri (G. Ljubijankic et al., J. DNA Sequencing and Mapping 3 (1992) 195–201) and Arthrobacter viscosis (M. Konstantinovic et al., (1993) EMBL databank entry L04471).

The use of recombinant DNA methods has enabled an increase of the production levels of commercially used penicillin acylases (Mayer et al., Adv. Biotechnol. 1 (1982) 83–86) and has enlarged the insight into the processing of these enzymes (G. Schumacher et al., Nucleic Acids Research 14 (1986) 5713–5727). The penicillin acylase of E. coli was found to be produced as a large precursor protein, which was further processed into the periplasmic mature protein constituting a small ($\alpha$) and a large ($\beta$) subunit. Cloning and sequencing of the Kluyvera citrophila acylase gene has revealed a close homology with the E. coli acylase gene (J. L. Barbero et al., Gene 49 (1986) 69–80). Also for Proteus rettaeri (G. O. Daumy et al., J. Bacteriol. 163 (1985) 1279–1281) and Alcaligenes faecalis (U.S. Pat. No. 5,168,048 and EP-A-453048, Gist-brocades) Penicillin G acylase a small and a large subunit has been described.

These publications neither teach nor suggest the instant invention.

Redesigning of specific activity of enzymes with the aid of protein-engineering techniques has been described.

Patent applications EP-A-130756 and EP-A-251446 describe the selection of residues and the mutagenesis of some of these residues in a certain group of serine protease with the purpose to alter the kinetic properties of these enzymes.

As these patent applications specifically deal with a certain type of serine proteases (the subtilisin type), these publications do not indicate which residues modulate the catalytic properties of Type-IIa Penicillin G acylases.

Wells et al. (Proc. Natl. Acad. Sci. USA 84 (1987) 5167) show an example for subtilisin. Bacillus licheniformis and B. amyloliguefaciens serine protease differ by 31% (86 residues) in protein sequence and by a factor of 60 in catalytic efficiency on certain substrates. By substituting 3 of the 86 different amino acids from the B. amyloliguefaciens sequence by the corresponding B. licheniformis residues the catalytic activity of the mutant enzyme was improved nearly 60 fold.

Wilks et al. (Science 242 (1988) 1541) describe how a lactate dehydrogenase was changed into a malate dehydrogenase by mutating glutamine 102 into arginine 102. In both cases, serine protease and lactate dehydrogenase, the inspiration for the modification proposal came from comparison with naturally occuring enzymes, which already showed the desired specificity. In the same way the specificity of cytochrome $p450_{15\alpha}$ was changed into the specificity of cytochrome $p450_{coh}$ by replacing Leu209 with Phe209 (Lindberg and Negishi, Nature 339 (1989) 632).

Patent application WO93/15208 describes a method for modifying the specificity and or efficiency of a dehydrogenase while retaining its catalytic activity, characterized in that it comprises: selecting an enzyme, the tertiary structure of which is substantially known or deduced; identifying at least one specificity and/or efficiency-related region; identifying or constructing unique restriction sites bounding the identified region in the DNA encoding therefor; generating a DNA sequence which corresponds to at least a portion of the identified region, except that the nucleotides of at least one codon are randomized, or selecting as a substitute for at least a portion of the identified region an alternative such region, which may itself be similarly randomized; using the generated or substitute DNA sequence to replace the original sequence; axpressing the DNA including the generated or substitute DNA sequence; and selecting for a desired modification so that the DNA coding therefor may be isolated. As dehydrogenases are in no way related to Penicillin G acylase, this patent application does not reveal the residues in the acylase which should be substituted to alter its kinetic properties.

Forney et al. (Appl. and Environm. Microbiology 55 (1989) 2550–2556; Appl. and Environm. Microbiology 55 (1989) 2556–2560) have isolated by cloning and in vitro chemical/UV random mutagenesis techniques E. coli strains capable of growing on glutaryl-L-leucine or D(−)-α-aminophenyl-acetyl-(L)-leucine. Penicillin acylase produced by the mutants hydrolyse glutaryl-L-leucine between pH and 6 or D(−)-α-amino-phenyl-acetyl-(L)-leucine at pH 6.5. Although it is supposed that the specificity shift of the Penicillin G acylase is due to one or more mutations in the acylase, the residue(s) involved nor the kind of mutation(s) were identified.

J. A. Williams & T. J. Zuzel (Journ. of Cell. Biochem. (1985) supplement 9B, 99) reported in an abstract of a poster presentation the modification of the substrate specificity of Penicillin G acylase by in vitro mutagenesis of a methionine. Although the abstract does not report the position of this methionine, from the poster it seemed to be possible to conclude that it involved position Met168 in E. coli acylase. However, this work did not reveal any details how substitution of this methionine relates to the observed specificity change. Prieto et al. (I. Prieto et al., Appl. Microbiol. Biotechnol. 33 (1990) 553–559) replaced Met168 in K. citrophila for Ala, Val, Asp, Asn, Tyr which affected the kinetic parameters for PenG and PenV deacylation. In addition mutants Lys375Asn and His481Tyr were made which showed hardly any effect on $k_{cat}$/Km.

J. Martin et al. analysed mutant Met168Ala in K. citrophila penicillin acylase and reported altered kinetic properties. (J. Martin & I. Prieto, Biochimica et Biophysica Acta 1037 (1990), 133–139). These references indicate the importance of the residue at position 168 in E. coli and K. citrophila for the specificity with respect to the acyl moiety. However, this work did not reveal any details how substitution of this methionine relates to the specificity change for the conversion of a desired substrate.

Wang Min reported mutagenesis of Ser177 in E. coli Penicillin G acylase to Gly, Thr, Leu, Arg but failed to obtain active acylases. (Wang Min et al., Shiyan Shengwu Xuebao hi (1991), 1, 51–54).

Kyeong Sook Choi et al. (J. of Bacteriology 174 (1992) 19, 6270–6276) replaced the β-subunit N-terminal serine in E. coli penicillin acylase by threonine, arginine, glycine and cysteine. Only when the N-terminal residue was cysteine the enzyme was processed properly and a mature enzyme but inactive enzyme was obtained. In addition chemical mutagenesis of the β-subunit N-terminal serine also led to severe/almost complete loss of activity (Slade et al., Eur. J. Biochem. 197 (1991) 75–80; J. Martin et al., Biochem. J. 280 (1991) 659–662).

Sizman et al. (Eur. J. Biochem. 192 (1990) 143–151) substituted serine 838 in *E. coli* for cysteine without any effect on the post-translational processing nor on the catalytic activity of the enzyme. In addition Sizman et al. made various deletion mutants of penicillin acylase. It showed that correct maturation of the acylase is very sensitive to mutagenesis. All β-subunit C-terminal deletion mutants were not expressed except for the mutant lacking the last three residues which, however, was very unstable. Insertion of four residues in *E. coli* at position 827 also failed to give active enzyme.

Prieto et al. replaced glycine 310 in *Kluyvera citrophila* penicillin acylase for glutamic acid. However, no active enzyme was obtained.

In EP-A-453048 it has been described how protein engineering may be used to alter the specificity of Type-IIa as well as Type-IIb acylase. However, the applied procedures are limited to the generation of libraries of randomly generated acylase mutants which have to be screened for a desired activity. Although by the method described in that patent application the number of amino acid positions which may be mutated has been reduced, the number of remaining positions is still large, so that position directed mutagenesis would be a laborious job. The present invention, however, gives a much more limited number of positions which are to be mutated. In addition amino acids at these positions are in direct contact with the substrate, which means that substitution will affect interaction with the substrate directly. Moreover the procedure leading to the present invention allows one to choose a particular amino acid substitution in order to obtain a desired effect for a specific substrate.

SUMMARY OF THE INVENTION

The present invention provides an isolated mutant prokaryotic Penicillin G acylase or its preenzyme or pre-proenzyme comprising:

a substitution at one or more selected sites of the positions corresponding to A139 to A152, B20 to B27, B31, B32, B49 to B52, B56, B57, B65 to B72, B154 to B157, B173 to B179, B239 to B241, B250 to B263, B379 to B387, B390, B455, B474 to B480 in *Alcaligenes faecalis* Penicillin G acylase or its pre- or preproenzyme; and an altered substrate specificity or altered specific activity relative to the corresponding wild-type unsubstituted Penicillin G acylase. Preferably, said isolated mutant prokaryotic Penicillin G acylase is originated from *Alcaligenes faecalis*.

Furthermore a nucleic acid sequence encoding said mutant acylase, a vector which comprises said nucleic acid sequence, and a microorganism host strain transformed with said vector have been provided for by the present invention.

According to another aspect of the invention a process of preparing said isolated mutant Penicillin G acylase has been provided, which process comprises:

culturing a microorganism host strain transformed with an expression vector comprising a nucleic acid sequence encoding a mutant acylase enzyme as defined above, whereby said mutant acylase is produced; and isolating said acylase.

Finally, a method for conducting an acylation or deacylation reaction has been provided, said process comprising contacting said isolated mutant Penicillin G acylase with a substrate for said acylase under conditions suitable for said reaction to occur. Preferably, a β-lactam compound is produced by said process.

Especially, a method for deacylating an acylated 6-amino penicillanic acid, an acylated 7-amino(desacetoxy) cefalosporanic acid or a salt or ester thereof to form the corresponding 6-amino penicillanic acid or 7-amino (desacetoxy)cefalosporanic acid or salt or ester thereof, respectively, which comprises contacting said 6-acylated or 7-acylated compound with a mutant acylase as defined above under conditions suitable for deacylation to occur, and a method for producing a semi-synthetic acylated 6-amino penicillanic acid, an acylated 7-amino(desacetoxy) cefalosporanic acid or a salt or ester thereof which comprises contacting a corresponding 6-amino or 7-amino β-lactam and an acylating agens with a mutant acylase as defined above under conditions suitable for acylation to occur, has been provided for.

BRIEF DESCRIPTION OF THE DRAWINGS

FIG. 2: Alignment of α(2a) (FIGS. 2A–2B) and (2β) (FIGS. 2C–2F) subunit of Type-IIa penicillin acylases mature enzymes. *Alcaligenes faecalis* (afae), SEQ ID NO:27 and SEQ ID NO:32, respectively), *E. coli* (ecol; SEQ ID NO:28 and SEQ ID NO:33 respectively), *Kluyvera citrophila* (kcit; SEQ ID NO: 29 and SEQ ID NO: 34, respectively), *Arthrobacter viscosus* (avis; SEQ ID NO: 30 and SEQ ID NO: 35, respectively). *Providencia rettgeri* (pret) *Providencia rettgeri* (pret; SEQ ID NO: 31 and SEQ ID NO: 36, respectively). Chain identifier A and B for α and β chain, respectively. An asterix denotes that the sequence contains the same amino acid at that position as the sequence from the *A. faecalis* acylase. For the *Providencia rettgeri* acylase the N-terminus and the C-terminus of the a-subunit not known. N-terminus β subunit Providencia rettaeri based on alignment with other acylases.

DETAILED DESCRIPTION OF THE INVENTION

Figure 1:
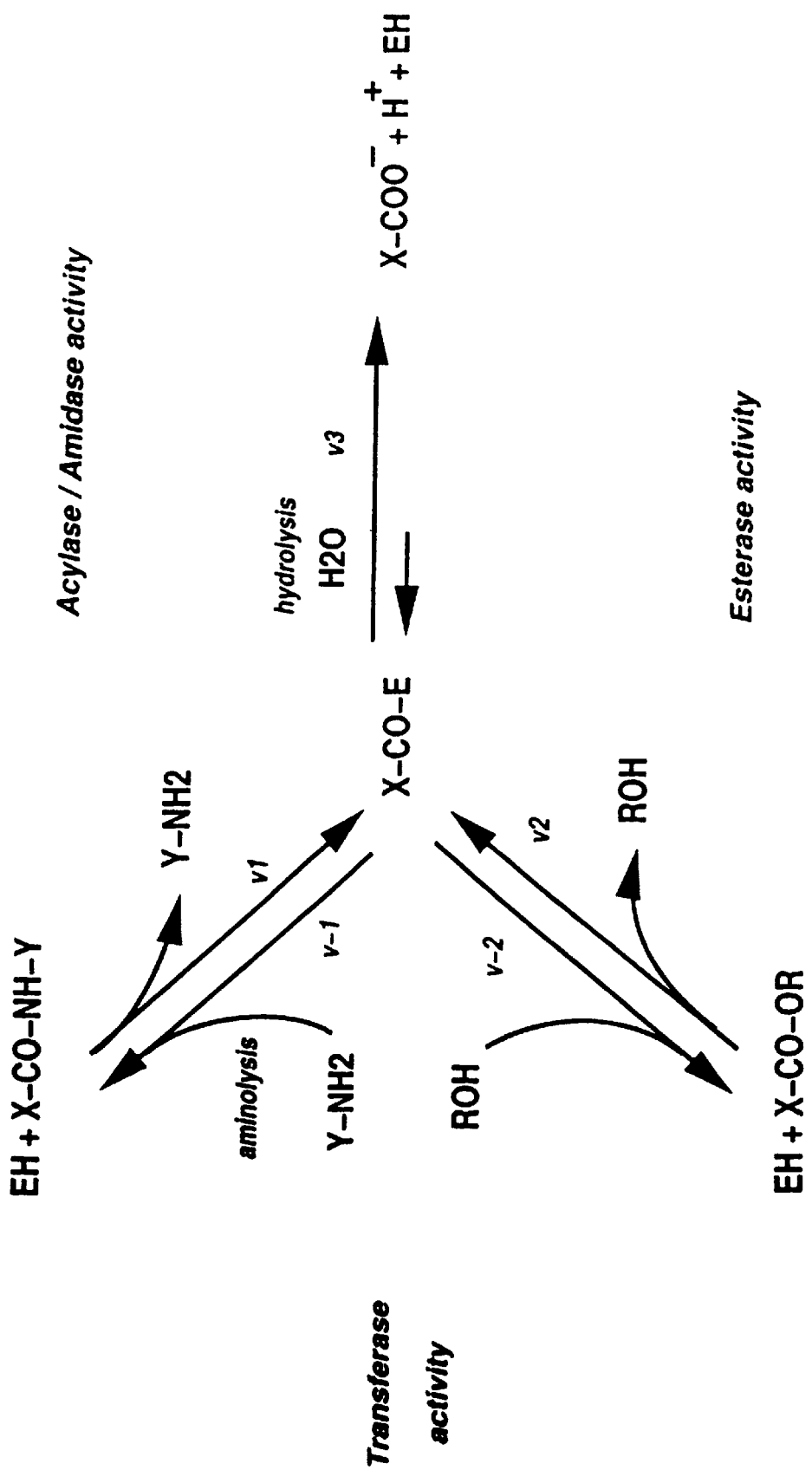
FIG. 1: Reaction scheme for Type-IIa penicillin acylases catalysed conversions. EH represents the enzyme where H stands for the proton which is transferred to the leaving group. X stands for the acyl moiety or side chain. Y is the compound to be acylated (acylation) or to be deacylated (deacylation). Compound X—CO—OR may also be a simple amide X—CO—NH2.

Hydrolysis/deacylation.

The present invention relates to the identification of residues which alter the kinetic properties of Penicillin G acylase, whereby said resulting Penicillin G acylase variant is more useful than said precursor Penicillin G acylase for the deacylation of primary aminogroups such as, for example, occur in penicillins and cephalosporins. These kinetic properties comprise specific activity, pH dependence of kinetic parameters, substrate specificity, stereo-selectivity and the ratio transferase to hydrolase activity.

Synthesis/acylation.

The present invention relates to Penicillin C acylase variants derived from precursor Penicillin G acylases via recombinant DNA methodology by changing at least one amino acid residue in said precursor, said Penicillin G acylase variant being more useful than said precursor Penicillin G acylase for the acylation of primary amino groups such as, for example, occur in β-lactam nuclei (preparation of semi-synthetic β-lactam compounds) and peptides.

The present invention relates to Penicillin G acylase variants derived from precursor Penicillin G acylases via recombinant DNA methodology by changing at least one amino acid residues in said precursor, said Penicillin G acylase variant being characterized by having a higher ratio transferase to hydrolase activity than said precursor Penicillin G acylase.

The Penicillin G acylases which are subject of this invention:

are isolated from prokaryotes;

are transcribed as a single peptide chain precursor;

are processed intracellularly after transcription resulting in a heterodimer with a small N-terminal domain (the α-domain) and a larger C-terminal domain (the β-chain). The molecular weight of the N-terminal domain is in the range 16–28 kDa. The molecular weight of the C-terminal domain is in the range 54–68 kDa;

may occur in solution as multimers of the αβ heterodimers;

have a serine at the N-terminus of the β-subunit.

Examples of such acylase producing microorganisms are certain strains of the species *Escherichia coli, Kluyvera citropthila, Providencia rettgeri*, Pseudomonas sp., *Alcaligenes faecalis, Bacillus mecaterium*, and *Arthrobacter viscosus*.

Several genes encoding Penicillin G acylases have been sequenced, viz. the genes from *E. coli, Kluyvera citrophila Alcaligenes faecalis, Proteus rettgeri* and *Arthrobacter viscosis*.

The alteration of the substrate specificity of Penicillin G acylases is achieved in such a way that the mutant enzymes are able to cleave or synthesize penicillin and cephalosporin derivatives possessing side-chains other than phenylacetyl, which is the natural side-chain of penicillin G. Examples of side-chains which are presently not significantly affected by Penicillin G acylases are acyl groups derived from the dicarboxylic acids succinic acid, glutaric acid, adipic acid and aminoadipic acid (the latter being the natural side-chain of CefC).

In another aspect the alteration of the specificity and activity of Penicillin G acylases is performed for side-chains which are already existing substrates for the said acylases. Using protein engineering the affinity for a substrate can be altered (e.g. increased, expressed by a lower $K_s$ for said substrate), the catalytic turnover may be altered (e.g. increased, expressed by a higher $k_{cat}$ for said substrate) or the second order rate constant may be altered (e.g. expressed by an altered $k_{cat}$/Km ratio, a parameter (which is usually used to compare specificity of an enzyme for different substrates). Relevant substrates in this aspect include acylated β-lactam derivatives such as penicillin V (PenV), ampicillin, amoxicillin, cefalexin, cefadroxyl or cefaclor. Moreover alteration of kinetic properties with respect to simple amides and esters of the acyl moiety are useful for obtaining increased accumulation of the acyl enzyme intermediate which may improve the yield in biosynthesi-s processes.

In another aspect the alteration of the specificity and activity of Penicillin G acylases is performed in order to increase the stereo specificity of Penicillin G acylases which results in enzymes which show improved enantiomeric excess in conversions with racemic mixtures of chiral compounds. Such property makes the Penicillin G acylase extremely useful for synthesis of enantiomerically pure semisynthetic antibiotics from racemic mixtures of phenylacetyl side chains or activated derivatives of the phenylacetyl side chains (e.g. phenylglycine-amides or esters therefrom, p-hydroxyphenylglycine-amides or esters therefrom, etc.) containing a chiral α-carbon due to the presence of an amino group (e.g. ampicillin, cefalexin, amoxicillin, cefadroxyl, cefaclor) or a hydroxyl group (cefamandol).

Apart from stereoselectivity for the acyl Cα position Penicillin G acylase exhibits also stereoselectivity for the amino part of the substrate. In case of amino acids the acylase requires the L-configuration at the Cα atom. In another aspect of the invention steroselectivity of the enzyme for the amino part of the substrate may be altered.

In another aspect of the invention the product inhibition is reduced with respect to the wild type enzyme. The desired variant maintains its initial high deacylation rate for a longer period during conversion resulting in a higher productivity. Examples of such inhibitory products are phenylacetate, phenoxyacetate, phenylglycine, p-hydroxyphenylglycine etc.

In another aspect of the invention the transferase activity of the enzyme is improved with respect to the hydrolases activity which makes the enzyme more useful in biosynthetic conversions. In particular variants with improved performance in the enzymatic synthesis of amoxicillin, ampicillin, cefaclor, cefadroxil, cefprozil, cephalexin, and cephradine are preferred embodiments.

Compared to the precursor acylase desired variants for biosynthesis are more easily deacylated by a β-lactam nucleus than by water (ratio aminolysis/hydrolysis). This may be obtained by improving the binding of the nucleophile relative to water Desired variants have altered esterase/ amidase ratio for particular substrates relative to the precursor enzyme i.e. for certain side chains the desired enzyme-shows a decreased amidase activity for amide derivatives of those side chains compared to the esterase activity for esters of the corresponding side chains.

In order to achieve alterations in the enzyme molecule, it is highly desirable to avail of the 3D structure of said enzyme. Sofar, no high-resolution, 3D-structures of acylases have been published.

Figure 2A:
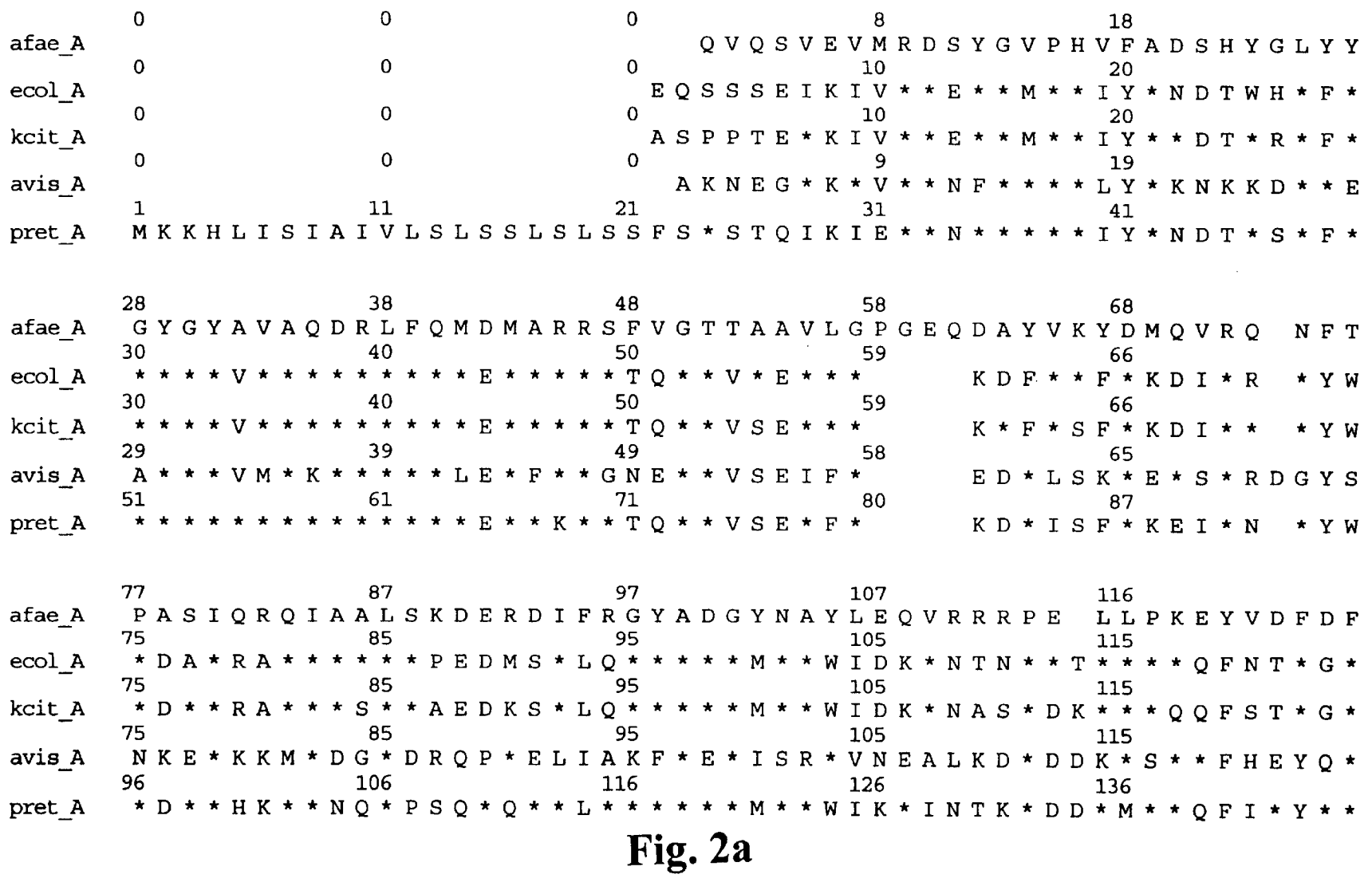

The known Penicillin G acylase gene sequence derived amino acid sequences were aligned in such a way that optimal homology was obtained. For sequence alignment the types of amino acids may be suitably used as parameters, based on identity but also on similarity. For example, serine is similar to threonine, aspartic acid is similar to glutamic acid, etc. The results are shown in FIG. 2 which gives an alignment of Penicillin G acylases from *Escherichia coli, Kluyvera citrophila, Alcaligenes faecalis, Providencia rettgeri* and *Arthrobacter viscosis*. The alignment of the five amino acid sequences reveals a significant homology between the Penicillin G acylases which points to a similar 3D-structure.

In an embodiment of the invention corresponding positions of other Penicillin G acylases, which are structurally homologous to *Alcaligenes faecalis* Penicillin G acylase can be substituted in the same way as *Alcaligenes faecalis* at the positions which are homologous to the positions in *Alcaligenes faecalis* Penicillin G acylase. The corresponding positions for these proteases may be obtained from the amino acid alignment as depicted in FIG. 2. In FIG. 2 the amino acid sequence of various acylases have been aligned, with respect to the sequence of the acylase of *Alcaligenes faecalis* (A. fae).

Although the selection of residues will be demonstrated here using the specific example of *Alcaligenes faecalis* Penicillin G acylase it is clear that due to homology similar substitution sites can be selected in Penicillin G acylases obtained from other species. The approach described would give rise, after amino acid replacement at corresponding positions in the Penicillin G acylase from the other species, to similar altered kinetic properties of other Penicillin G acylase also. By similar is meant the kind of effect which the substitutions have on the kinetic parameters change.

In an embodiment of the invention genes encoding known Penicillin G acylases, for example, Penicillin G acylases from *Escherichia coli, Kluyvera citrophila, Alcaligenes faecalis, Providencia rettgeri* and *Arthrobacter viscosis* or any other organism producing such enzymes, are mutated in such a way that the enzymes obtain an altered specificity for their substrates.

In an embodiment of the invention, genes encoding the structurally homologous Penicillin G acylases, for example, Penicillin G acylases from *Escherichia coli, Kluyvera citrophila, Alcaligenes faecalis, Providencia rettgeri* and *Arthrobacter viscosis*, are mutated in such a way that the enzymes obtain an altered substrate specificity or new specificity.

Changes in substrate specificity demonstrated in the present invention include all combinations of increase and decrease of $V_{sax}$ and $K_s$ for both penicillin and cephalosporin derivatives. A person skilled in the art will understand that this encompasses the changes in other kinetic parameters. Furthermore, the specificities for other substrate will inherently be changed also. The proposed rules for changing the substrate specificity are not restricted to the mentioned substrates, they can be applied to other substrates among these are phenylacetyl or phenoxyacetyl derivatives of amino acids, aminoalkylphosphonic acids, primary and secondary alcohols, cefamicines, nocardicines, monobactams, nucleic acids, carbohydrates, peptides.

As the mechanism of maturation of Penicillin G acylase from a one-peptide chain to an active dimer is still obscure another important aspect of the invention shows that it is possible to replace active site residues in Penicillin G acylase without affecting the maturation of the acylase.

The underlying invention to provides a methods to recruit novel specificities for Type-IIa Penicillin G acylases. For the introduction of point mutations a rational approach is taken, relying on the application of protein crystallography, molecular modelling and computational methods, enzymology and kinetics, molecular biology and protein chemistry techniques. The strategies for the identification of targeted mutations in Penicillin G acylase are innovative in a sense that it is recognized that point mutations may affect several different properties of the protein structure at once. In particular some point mutations may prevent proper folding or correct processing resulting in an inactive enzyme. Therefore, although the described strategies make use of well established structure-function relationships, they also provide a rational way to avoid or correct unwanted alterations of secondary properties.

According to the present invention specific amino acid positions to be substituted have been identified within the available 753 positions in the Penicillin G acylase molecule from *A. faecalis*, and the effect of such mutations on the particular properties of the enzyme. Thus A139 to A152 [SEQ ID NO:27], B1, B2, B20 to B27, B31, B32, B49 to B52, B56, B57, B65 to B72, B154 to B157, B173 to B179, B239 to 241, B250 to B263, B379 to B387, B390, B455, and [SEQ ID NO:32] B474 to B480 are identified as important positions with regard to the catalytic properties of the enzyme. various specific residues have been identified as being important with regard to substrate specificity. These residues include: A:Met143, A:Arg146, A:Phe147, A:Thr150 [SEQ ID NO:27], B:Pro22, B:Phe24, B:Gly25, B:Tyr27, B:Tyr31, B:Thr32, B:Pro49, B:Tyr52, B:Leu56, 3: Phe57, B:Gly66, B:Ala67, B:Thr68, B:Ala69, B:Gly70, B:Pro71, B:Trp154, B:Val157, B:Met173, B:Ile175, B:Ser176, B:Ile177, B:Trp179, B:Asn239, B:Trp240, B:Thr251, B:Thr253, B:Tyr254, B:Tyr255, B:Trp256, B:Arg261, B:Met262, B:Asn379, B:Pro380, B:Gly381, B:Ser382, B:Ile383, B:Asn384, B:Lys390, B:Phe455 B:Thr477, B:Glu478 [SEQ ID NO:32]. The identification of these positions, including those yet to be mutated is based on a 3D model of the *A. faecalis* Penicillin G acylase (see FIGS. 4a and 4b).

Selection procedure for residues which alter desired properties.

Desired rrorerties are altered catalvtic properties, altered specificity, improved transferase activity The crucial first step for performing site-directed mutagenesis with the object to alter kinetic properties of an enzyme is to obtain a 3D structural model of the subject Penicillin G acylase complexed with the β-lactam compound of interest. This can be done in two ways, namely via a direct experimental approach, or via an indirect approach using molecular modeling.

The direct approach.

Determine the 3D-structure of the subject Penicillin G acylase in complex with the β-lactam compound of interest by X-ray diffraction. However, when the particular β-lactam compound is a substrate for the particular Penicillin G acylase, it will be converted into the products of the reaction in the time-course of the structure determination experiment. In such cases cryo-crystallography may be applied or very fast data-collection techniques such as Laue diffraction. With conventional techniques binding of fragments of the substrate can reveal the binding site. As an alternative the substrate can be modified in such a way that the scissile bond in the substrate cannot be cleaved by the enzyme (e.g. phosphoamide or phosphonate bonds instead of a peptide bond in a peptide, D. E. Tronrud et al. Science 235 (1987) 571–574). However, an elegant method is to replace one or more of the catalytic residues resulting in an inactive enzyme which cannot convert the substrate but can still bind the substrate. For example, in Penicillin G acylase the β-subunit N-terminal serine may be mutated to cysteine. When it is not possible to obtain a 3D structure of the subject acylase complexed with the desired β-lactam derivate by experiment, conventional computer modelling techniques can be applied. Chemical modification studies and site directed mutagenesis revealed the N-terminal serine of the β-subunit to be critical for catalytic activity. Surprisingly calculation of the accessible residues in *A. faecalis* Penicillin G acylase model revealed a deep hydrofobic cavity near the β-subunit N-terminal serine which accomodates the Penicillin G phenylacetyl side chain perfectly while positioning the β-subunit N-terminal serine in an ideal position for nucleophilic attack at the peptide carbonyl of PenG.

In the next step the β-lactam moiety was positioned while keeping the phenylacetyl group fixed in its binding pocket. Atomic overlap between substrate and enzyme is avoided as much as possible while positive interactions are maximized. Relevant positive interactions which contribute to binding are hydrogen bonding, electrostatic interactions and favourable VanderWaals contacts. The contribution of hydrofobic interactions can be estimated from the calculation of the accessible non-polar surface which is buried by binding the substrate to the enzyme.

In addition to manual manipulation of the substrate computational techniques are applied to optimize the substrate-enzyme complex. Molecular mechanics techniques such as energy minimization and molecular dynamics are very useful. Suitable forcefields for proteins such as CVFF, AMBER, CHROMOS may be used.

The final model is used to survey the environment of the PenG molecule. This survey supplies crucial insight in the residues which interact with the PenG molecule (see example 1). In addition it provides insight which residues interact with which parts of the substrate. This information provides the molecular biologist with only a limited set of residues compared to the overall size of the acylase (753 residues) which can be used to modulate the catalytic properties of Penicillin G acylase. Now a person skilled in the art of site specific mutagenesis just has to focus on only a limited number of residues, substitute these residues and select for desired altered catalytic properties.

In general when a substrate binds to the free enzyme it causes lo some strain in the enzyme and in the substrate. Such strain can be relieved by molecular mechanics calculations allowing atoms to shift position with respect to each other. Comparison of the enzyme-substrate complex with the free enzyme will indicate which residues are affected most by substrate binding. Parameters which are important in this aspect are RMS positional shifts of residues with respect to the free enzyme, changes in the electrostatic environment around residues with respect to the free enzyme, hydrogen bond formation or the change of free energy of residues. Electrostatic potentials may be calculated using a program such as DELPHI (Biosym Technologies). As residues which are affected by binding of the substrate will in turn affect the binding of the substrate, substitution of these residues is a preferred embodiment of this invention taking into account the restrictions for substitution of amino acids in proteins structures. Substitution that should be avoided are those substitutions which are expected to affect typical structural arrangements such as: salt bridges, packing of helices, stabilization of helices by keeping a negative charge at the start of a helix, initiation of helices, e.g. prolines at the start of a helix, Phi-psi angles which are outside the allowed region for the residue that is going to be inserted.

The proposed rules for changing the activity for a certain substrate are not restricted to PenG, they can be applied to other substrates as well. For example, instead of PenG a cephalosporin molecule may be taken such as CefG, which has the phenylacetyl side chain in common with PenG. In this case the whole modelling procedure may be repeated as described above. However, we prefer to substitute in the computer the 6-APA moiety of the PenG molecule which is complexed to the Penicillin acylase for the 7-ADCA moiety and subsequently refine the structure by molecular mechanics. Comparison of the structures of Penicillin G-acylase complex with the CefG-acylase complex will establish the residues which have been affected by modification of the substrate. Residues which are affected by modification of PenG will in turn modulate the binding of the modified substrate. Substitution of such residues is a preferred embodiment in order to alter the kinetic properties of such a modified substrate with respect to PenG.

For some modifications of the substrate it turns out to be impossible to relieve the strain caused by the modification without effecting the position of the scissile peptide bond with respect to the β-subunit N-terminal serine nucleophile. In such cases the distance from the β-subunit N-terminal serine nucleophile to the carboxyl carbon of the scissile bond is constrained within the range 2 to 3 Å during energy minimization and molecular dynamics. In addition computational mutagenesis of the acylase is performed to reduce undesirable interaction with the substrate and increase benificial interaction (relevant interactions have been discussed above). However, when the binding of the modified substrate is unwanted and should be prohibited, undesirable interaction may even be increased at such positions by site directed mutagenesis. This approach establishes a limited number of mutations which will alter the kinetic properties in a desired direction. Subsequently such limited number of mutations can be made and tested for the desired properties.

Desired modifications imply substitution of the PenG side chain benzene ring by a five- or six-membered hydrocarbon ring (e.g. cyclohexadienyl, cyclohexenyl, cyclohexyl), optionally substituted either by a five-membered heterocycle containing one to four heteroatoms (N, O, or S) (e.g. thienyl, furyl) which heterocycle may be optionally substituted, or by an aliphatic side chain (e.g. propyl, butyl, pentyl, heptyl) which may be optionally substituted. Side chains may have one or more substituent including but not limited to hydroxyl, halogen, alkyl, alkoxyl, carboxyl, nitro, amino, and the like. In addition the phenylacetyl side chain may be substituted at the a-position resulting in a D- or L-stereoisomer. Substituent may include but are not limited to hydroxyl, halogen, alkyl, alkoxyl, carboxyl, nitro, amino, and the like. Selecting residues which affect the selectivity of the acylase with respect to stereoisomers is a preferred embodiment of the invention. Examples of desired side chains are, for example, 2-thienylacetyl, α-hydroxyphenylacetyl, p-hydroxyphenylacetyl, p-hydroxyphenylglycyl, phenylglycyl, succinyl, glutaryl, adipyl, α-aminoadipyl etc.

Beside modification of the β-lactam side chain also the β-lactam moiety itself may be subject to modification. As exemplified above the 6-APA moiety may be replaced by 7-ADCA. Instead 7-ACA may be taken. In addition the β-lactam moieties may be substituted at one or more positions. In particular the cephalosporins may contain substituents at the sulphur, at the 3-position or at the 4 position. For example, the 3-position may be substituted with a halogen atom, a methoxy, a methyl or a methylene bonded via a bridging atom O, N, or S to an organic moiety or five- or six membered (hetero) cyclic group which may optionally be substituted. At the 4-position the carboxylic acid substituent may be modified with various carboxyl protecting groups. Furthermore the given method allows also to analyze the structural requirements for acylases which may convert β-lactam moieties such as carbapenems, nocarcidines, monobactams or derivatives derived therefrom.

For the purpose of biosynthesis the interaction of the acylase with reactive derivatives of desired side chains may be modulated. Useful examples of such side chain derivatives are alkyl esters, amides and acylated amino acids.

The process of the invention can be used to select those position in type-II Penicillin G acylases at which amino acids should be substituted in order to affect the interaction with penicillins/cephalosporins and their derivatives which results in enzymes with altered kinetic properties. Position directed mutagenesis will provide a limited number of variants which can be easily tested for improved conversion of the desired substrate. This in contradiction to the random approach which results in an enormous number of mutants which is very difficult to handle.

Materials and methods

Mutagenesis.

For the construction of mutant acylase genes the overlap extension polymerase chain reaction has been used essentially as described by Ho et al. (Gene 77 (1989) 51–59). Mutant oligo's were used in combination with flanking oligo's to generate DNA amplification products harbouring the desired mutation. This mutant DNA fragment was exchanged with a corresponding restriction fragment of the wild type gene, e.g. pMcAF. The mutant oligo's have been designed to harbour single and multiple mutations.

Site-directed mutagenesis of cloned DNA fragments can also be carried out as described by Stanssens (Stanssen et al., Nucleic Acids Res. 17 (1989) 4441–4454) with the aid of the phasmid pMa/c system. Suitable gapped duplex molecules of acylase genes were constructed. With specific mismatch oligonucleotides site directed mutations were introduced. Expression of acylase genes was obtained in *E. coli* WK6 either from the homologous expression signals or from the *E. coli* lac, tac or trp promoter (De Boer et al., Proc. Natl. Acad. Sci. USA 80 (1983) 21–25). 'Spiked' oligo mutagenesis and random mutagenesis of the gapped DNA was performed as described (EP-453048).

Both PCR overlap extension and gapped duplex have been combined with another type of mutagenesis: targeted random mutagenesis (TRM).

This comprises the inclusion of two or more bases at the codon for a specific amino acid during the synthesis of the oligonucleotide. In doing so, a mutagenic oligonucleotide which can generate all other possible amino acids at a chosen codon can be synthesized. A single amino acid position or a combination of several positions can be mutagenized in that way.

Selective media.

Selective media for phenylacetyl L-leucine ('fal' ) were prepared as described by Garcia (Garcia et al., J. Biotech. 3 (1986) 187–195). Minimal plates are as follows: M63 minimal agar, 2 g/l glucose, 1 mg/l thiamine, 10 mg/i L-proline and the appropriate antibiotic (50 µg/ml chloramphenicol (cap) or 25 µg/ml ampicillin (amp)). For selections on side-chain specificity (e.g phenylacetyl, phenoxyacetyl, phenylglycyl, p-hydroxyphenylglycyl, adipyl or α-aminoadipyl) of acylases 100 µg/l of the corresponding acyl L-leucine was included into minimal plates. Transformants or mutants of *E. coli* HB101 (Leu) growing exclusively in the presence of the acyl L-leucine are considered to harbour an acylase gene with the desired specificity. Instead of leucine the amino acid moiety of the selective substrate may also be varied. In such case a suitable auxotrophic mutant of *E. coli* was used for selection. For example, selection on the substrate N-adipyl-L-leucine was carried out with *E. coli* strain PC2051 as a host (obtained from Phabagen, Utrecht, the Netherlands). The special screenings substrates were purchased from LGSS, Transferbureau Nijmegen, the Netherlands.

Phenylacetyl amide was added to a final concentration of 15 mM to minimal M63 medium supplemented with 0.2% of either succinate, glycerol or glucose as carbon source, and thiamine (1 µg/ml), L-proline (10 µg/ml), and the appropriate antibiotic. All salts in the basal medium were replaced by the corresponding salts containing either $Na^+$ or $K^+$ ions in order to ensure selective growth on the amide. Amides with the desired side-chains were purchased from commercial suppliers or prepared according to standard techniques. *E. coli* strains JM101, WK6, HB101, PC2051 and PC1243 were used as hosts to select for mutant genes with specificity for the selective amides.

Isolation and purification wild type and mutant acylases.

Cells were harvested by centrifugation and resuspended in 10 mM sodium phosphate buffer pH 7.4 containing 140 mM NaCl. The cells were disrupted through sonification (6×20 sec, 100 W, 100 mm bar, Labsonic 1510: after every 20 seconds the cells were cooled on ice for 30 seconds). Subsequently, the suspension was centrifugated. The sonification procedure was repeated with the resuspended pellet and finally the cell debris was removed by centrifugation. Via ultra-filtration the supernatant is extensively washed with milli-Q water and subsequently with the starting buffer for the Q-Sepharose: 20 mM $NaH_2PO_4.H_2O$ pH 7.0 +azide. Filter system supplied by Filtron with a Verder pump. The cut off of the filter is 5 Kda. After ultrafiltration the sample is diluted with milli-Q until the conductivety is less or equal to the starting buffer.

The sample is applied to a Q-sepharose column equilibrated with 20 mM $NaH_2PO_4.H_2O$ pH 7.0+0.02% azide (conductivity=2.60 mS) and run at a flow of 20ml/min. The gradient (in 50 min to 100% 20 mM $NaH_2PO_4.H_2O$ +0.5M NaCl pH 7.0+0.02% azide) was started after having washed the column thoroughly with starting buffer. Detection as at 280 nm. In a next step the acylase was further purified on Hydroxylapetit (HA-ultragel IBF) equilibrated with 10 mM $NaH_2PO_4.H_2O$ +10 µM $CaCl_2$+0.02% azide pH 6.8. The column is run at 4ml/min. The acylase elutes in equilibration buffer. The column is regenerated with 350 mM $NaH2PO4.H20$+10 µM $CaCl_{2+0.02}$% azide pH 6.8. In case very pure protein is required the first column step (Q-sepharose) is repeated with a longer column.

Protein concentration.

The total protein content during isolation and purification was determined using the Bradford method with BSA standard. The protein concentration of pure *A. faecalis* Penicillin G acylase can be calculated from the molar extinction coefficient at 280 nm. The molar extinction coefficient was calculated using the amino acid composition. The molar extinction coefficient calculated was 161210 $M^{-1}cm^{-1}$ which corresponds with an OD of 1.87 for 1 mg/ml at a 1 cm path.

The concentration of catalytic centres of the wild type enzyme was determined by titration of penicillin acylase with Phenyl-methylsulphonylfluoride (PMSF) dissolved in isopropanol at different concentrations. In addition the acylase content of the final acylase samples was determined with analytical reversed phase chromatography. Column: RP300 7micron 20×2.1 mm. Injection volume 5 µl. The protein was eluted using a linear gradient starting with 100% A (water) and changing to 80% B (70% acetonitrile in water) in 45 minutes. The acylase is eluted in two peaks corresponding to the α and β subunit. Because the acylase content of the samples which was calculated from the active site titration experiments was found to be in line with the acylase content calculated from HPLC data, acylase mutants which did not titrate very well with PMSF were applied to RP-HPLC in order to determine the acylase content.

Penicillin acylase activity was assayed using NIPAB as a substrate.

Enzyme assays.

In order to determine enzymatic activity the acylases were incubated with substrate at room temperature in buffered solution. In case β-lactamase impurity was expected to be present in the enzyme preparations, 1.0 mM -lactamase inhibitor 6-bromo-penicillanic acid was added to the assay. The reactions were stopped by adding an excess PMSF. For some mutants which were less sensitive to PMSF inhibition, the reactions were stopped by adding 0.5 M HCl or 0.5 M acetic acid until the pH was between 3 and 4. When reactions were subsequently analysed by HPLC, the reactions were stopped by dilution with the correponding elution solvent (see table 1). In addition substrates were incubated under assay conditions in absence of enzyme. If necessary enzyme assays were corrected for non-enzymatic hydrolysis The composition of the reaction mixtures was determined by high-performance liquid chromatography (HPLC)(table 1). Concentrations were determined by using standards of known concentration.

TABLE 1

Procedures for analysis of the composition of enzyme reaction mixtures using high-performance liquid chromatography (HPLC). Reactions were stopped by diluting the reaction mixture with the appropriate solvent which is indicated in the left column. Detection at 214 nm. Flow 1 ml/min. SDS = Sodium dodecylsulphate.

| Sample | Column | Solvent |
|---|---|---|
| PenG 1:1 with solvent A | CP-Microspher C18 (Chrompack, cat. no 28410) | A: 30% acetonitrile in 0.1 M $KH_2PO_4$ pH 3 with 0.75 g/l SDS |
| PenV 1:1 with solvent A | CP-Microspher C18 | A: 30% acetonitrile in 0.1 M $KH_2PO_4$ pH 3 with 0.75 g/l SDS |
| CefG 1:1 with solvent A | CP-Microspher C18 | A: 20% acetonitrile in 0.05 M $KH_2PO_4$ pH 3 with 0.68 g/l SDS |
| Ampicillin 1:3 with solvent A | CP-Microspher C18 | A: 15% acetonitrile in 0.05 M $KH_2PO_4$ pH 3 with 0.68 g/l SDS during 6 min; B:A with 50% acetonitrile during 16 min. |
| PGA 1:1 with solvent A | CP-Microspher C18 | A: 25% acetonitrile in 0.05 M $KH_2PO_4$ pH 3 with 0.68 g/l SDS |
| Amoxicillin 1:2 with solvent A | Chromspher C18 (Chrompack, cat. no 28267) | A: 25% acetonitrile in 0.012 M $KH_2PO_4$ pH 2.6 with 2 g/l SDS |
| Ampicillin, PGA, PG, 6APA mixtures | Chromspher C18 | A: 30% acetonitrile in 0.005 M $KH_2PO_4$ pH 3.0 with 0.68 g/l SDS |

At low concentration formation of 6-APA, 7-ACA or 7-ADCA was measured by titration with fluorescamine. Concentrations were determined by measuring the fluorescence at 475 n=after 390 nm excitation. In addition the concentrations of 6-APA, 7-ACA, 7-ADCA were determined using the indicator reaction with p-dimethylaminobenzaldehyde. Formation of a Schiff base was followed at 415 nm (K. Balasingham st Al., Biochmica et Biophysica Acta 276 (1972) 250–256).

In a continuous assay Penicillin G acylase was assayed spectro-fotometrically with the chromogenic substrate NIPAB [6-nitro-3-phenylacetamido-benzoic acid]. The liberation of 3-amino-6-nitrobenzoic acid was monitored by measuring the extinction at 405 nm in a Kontron 610 kinetic spectrofotometer. Measuring maximal rate, the assays were performed at 25° C. using 20 mM $NaH_2PO_4.H_2O$ at pH 7.5 with 20 mM NIPAB and 100 µl enzym solution (at a proper dilution). Initial rate measurements were performed with varying concentration of NIPAB.

The kinetics of enzymatic hydrolysis of PenG, PenV, CefG were also studied by alkaline titration (0, OlM KOH), using a Radiometer pH-stat. All experiments were carried out in a buffer free medium.

Initial rate measurements were performed with excess substrate over the enzyme. Catalytic parameters were derived from least-squares fitting of the measured initial rates plotted for various substrate concentrations according to the Michaelis-Menten equation.

Deacylation of the acylated L-amino acids which were used in the screening was performed by incubation of the acyl amino acids with enzyme. Subsequently the deacylated amino acids were labeled by a method based on reaction with o-phthaldehyde and mercaptoethanol and quantitated using reversed phase HPLC.

Synthesis reactions were carried out in a pH-stat or in a buffered solution. Typical conditions used: lOmM PGA, pH 7.0, 30° C. and 30 mM 6-APA. Products were analysed and quantitated by HPLC.

The reaction conditions under which the acylases were tested depend on various parameters, in particular the reagents, reaction time, temperature and enzyme concentration. The preferred conditions can be readily determined by the man skilled in the art. Generally, the reaction temperature may vary between 0° and 40° C.

Examples of semi-synthetic β-lactams that may be produced by the application of the mutant acylase of this invention are amoxicillin, ampicillin, cefaclor, cefadroxil, cefprozil, cephalexin, and cephradine.

The acylating agens may be a derivative of D(-)-phenylglycine, D(-)-4-hydroxyphenylglycine or D(-)-2,5-dihydro-phenylglycine such as a lower alkyl (methyl, ethyl, n-propyl or isopropyl) ester or an amide which is unsubstituted in the —CONH2 group.

Generally, the reaction temperature of the process of this invention may vary between 0° C. and 35° C.

EXAMPLES

Example 1

Exploring the environment of Penicillin G in the Penicillin G-acylase:PenG complex and identification of residue position which affect the catalytic properties of Penicillin G acylase.

The solvent accessible surface of the *A. faecalis* Penicillin G acylase active site was calculated using the Connolly algorithm. The probe size was 1.4 Å. Contouring of the accessiblity using Molecular Graphics revealed a deep hydrofobic cavity near the β-subunit N-terminal serine which was accessible from the solvent. Computer aided docking showed that the phenylacetate fits perfectly in this cavity. After positioning the phenylacetate in the cavity the β-subunit N-terminal serine is in an ideal position for nucleophilic attack at the peptide carbonyl of PenG.

In the subsequent step the β-lactam moiety is positioned while keeping the phenyl-acetyl group fixed in its binding pocket. Atomic overlap between substrate and enzyme is avoided as much as possible while positive interactions are maximized. Relevant positive interactions which contribute to binding are hydrogen bonding, electrostatic interactions and favourable VanderWaals contacts. Hydrophobic interaction was estimated from the accessible non-polar surface which is buried by binding the substrate to the enzyme.

After manual manipulation of the substrate additional computational techniques were applied to optimize the substrate-enzyme complex. Energy minimization and molecular dynamics of the complex were performed using the CVFF forcefield (Biosym Technologies). Minimization was performed in a number of discrete steps. Minimization stopped when first derivative energy less than 0.01 kca1/mol First the complexed PenG substrate was minimized while keeping the acylase atoms fixed. The distance serine B1 OG to PenG scissile carbonyl carbon was constrained between 2 and 3.5 Å.

No charges were considered.

Then hydrogen atoms of the acylase were allowed to move.

Subsequently the side chains which have at least one atom within 12 Å of the PenG substrate are allowed to shift while still keeping the backbone fixed. The distance serine B1 OG to PenG scissile carbonyl carbon was still constrained between 2 and 3.5 Å. No charges considered.

After optimization of the side chains also the main chain was allowed to move. First movement was restricted due to tethering the main chain atoms. Gradually the tethering force was relaxed.

Figure 4A:
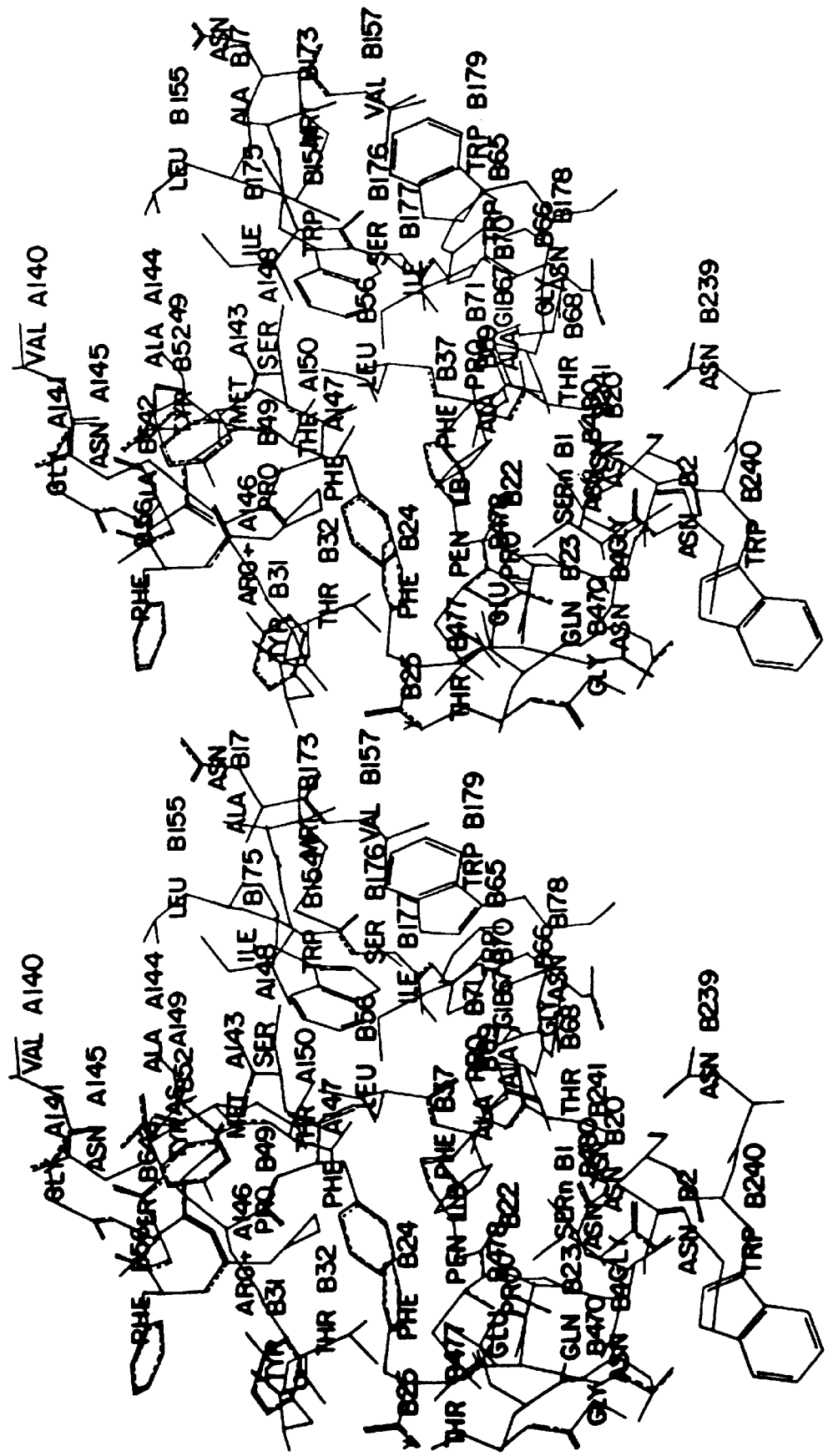
FIG. 4a: Stereo picture of the active site *A. faecalis* PenG acylase around phenylacetyl moiety.

The initial model obtained in this way was used to analyse the environment of the PenG molecule. FIG. 4a shows the residues which form the binding site of the phenylacetate moiety of the PenG substrate. Chain segments involved comprise: A139 to A152 [SEQ ID NO:27], B1, B2, B20 to B25, B31, B32, B49 to B52, B56, B57, B65 to B72, B154 to B157, B173 to B179, B239 to B241 and B476 to B480 [SEQ ID NO:32] Table 2 reviews residues which have at least one atom within 8 Å from the PenG phenylacetyl moiety. This survey supplies insight in the residues which interact with the side chain moiety of the penicillin molecule. Essential residues for catalysis should not be replaced as substitution leads to severely crippled or inactive acylases. These residues comprise: B:Ser1, B:Gln23, B:Asn241

Residues in *A. faecalis* Penicillin G acylase which are of particular interest for binding penicillin side chain are: A:Met143, A:Phe147, [SEQ ID NO:27], B:Pro22, B:Phe24, B:Tyr31, B:Thr32, B:Pro49, B:Tyr52, B:Leu56, B:Phe57, B:Gly66, B:Ala67, B:Thr68, B:Ala69, B:Gly70, B:Pro71, B:Trp154, B:Val157, B:Met173, B:Ile175, B:Ser176, B:Ile177, B:Trp179 [SEQ ID NO:27].

Figure 4B:
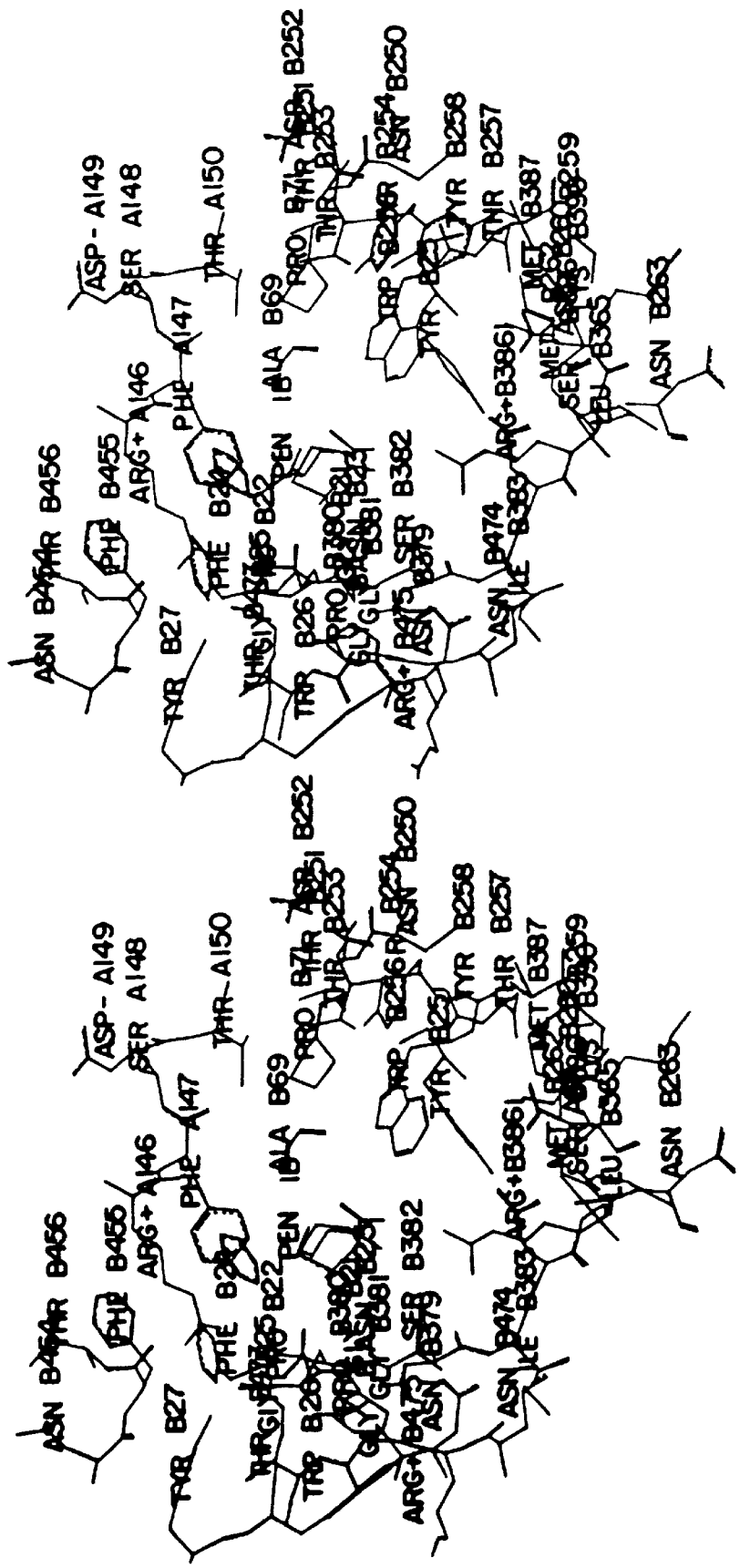
FIG. 4b: Stereo picture of the active site *A. faecalis* PenG acylase around the 6-ACA moiety.

In addition the environment of the β-lactam moiety 6-APA was mapped. Table 3 reviews residues which have at least one atom within 8 Å from an atom in the PenG 6-APA moiety. FIG. 4b shows the residues which form the binding site of the β-lactam moiety of the PenG substrate. Chain segments involved comprise: A146 to A150 [SEQ ID NO:27] B21 to B27, B71, B250 to B263, B379 to B387, B390, B454 to B456, and B474 to B477 [SEQ ID NO:32]. FIG. 4b shows the *A. faecalis* Penicillin G acylase active site focussing on the residues around the β-lactam moiety Residues in *A. faecalis* Penicillin G acylase which are of particular interest for binding the penicillin β-lactam part are: A:Arg146, A:Phe147, A:Thr150, [SEQ ID NO:27] B:Gly25, B:Tyr27, B:Ala69, B:Pro71, B:Thr251, B:Thr253, B:Tyr254, B:Tyr255, B:Trp256, B:Arg261, b:Met262, B:Asn379, B:Pro380, B:Gly381, B:Ser382, B:Ile383, B:Asn384, B:Met387, B:Lys390, B:Thr477, B:Glu478 [SEQ ID NO:32].

TABLE 2

Environment of the phenylacetyl moiety in Penicillin G Acylase complexed with PenG

Figure 3:
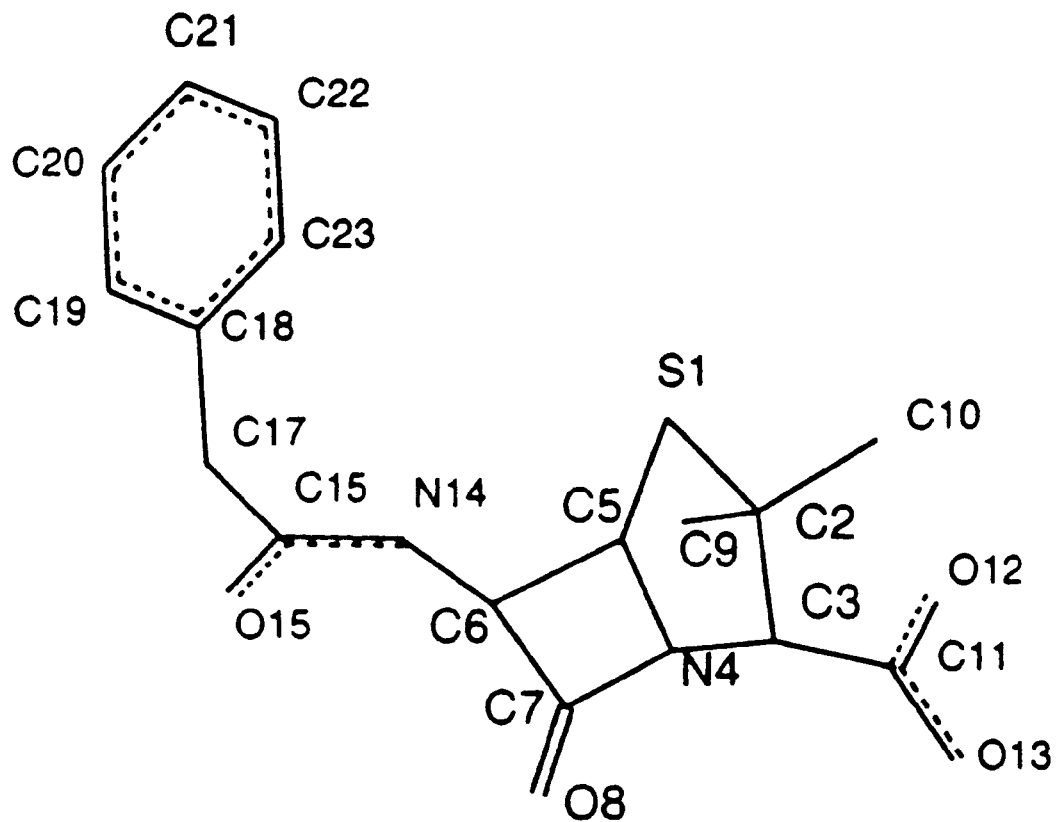
FIG. 3: Atom names PenG referring to nomenclature used in tables 2 and 3.

| PenG atoms (FIG. 3) | Atoms in the acylase within a certain distance range from PenG. Only closest atoms given. Distances in Å. Atom indication: chain-residue number:atom | | | | |
|---|---|---|---|---|---|
| | 3–4 | 4–5 | 5–6 | 6–7 | 7–8 |
| C15 | B1:OG<br>B23:O | A147:CZ<br>B69:CB<br>B241:ND2 | B22:C<br>B24:CD2<br>B68:C | B2:N<br>B21:O<br>B67:O<br>B382:OG | A147:CZ<br>B25:N<br>B70:N<br>B71:CG<br>B240:CD1<br>B256:CZ2<br>B261:CZ<br>B477:OG1 |
| O16 | B1:CB<br>B69:N<br>B241:ND2 | A147:CE2<br>B23:O<br>B68:CA | | B2:N<br>B21:O<br>B22:CA<br>B24:CE2<br>B67:O<br>B70:N<br>B71:CG | B176:O<br>B177:CD1<br>B178:ND2<br>B239:OD1<br>B240:CD1<br>B256:CZ2<br>B261:CZ<br>B382:OG |
| C17 | B1:OG<br>A147:CE2<br>B23:O<br>B24:CD2 | B22:C<br>B69:CB | B68:CA<br>B241:ND2 | A146:CZ<br>B21:O<br>B25:N<br>B57:CZ<br>B67:O | A143:SD<br>B2:N<br>B31:CE2<br>B56:CD2<br>B70:N<br>B177:CD1<br>B477:OG1 |
| C18 | B24:CE2 | A147:CZ<br>B1:CB<br>B22:CB<br>B23:O<br>B68:CA<br>B69:CB | B57:CZ<br>B67:O<br>B241:ND2 | A143:SD<br>B21:O<br>B56:CD2<br>B177:CD1 | A146:CZ<br>B2:N<br>B20:ND2<br>B31:CE2<br>B49:CG<br>B70:N<br>B177:CG1<br>B477:OG1 |
| C19 | A147:CG<br>B24:CE2<br>B69:N | B1:OG<br>B68:C | A143:SD<br>B22:CB<br>B23:O<br>B56:CD2<br>B67:C<br>B177:CD1<br>B241:ND2 | B57:CZ<br>B70:N | A142:O<br>A146:C<br>B31:CE2<br>B49:CG<br>B71:CD<br>B154:CZ2<br>B176:O<br>B178:N |
| C20 | B69:N | A143:SD<br>A147:CB<br>B24:CE2<br>B56:CD2<br>B67:CB<br>B68:C<br>B177:CG2 | B1:OG<br>B22:CB<br>B57:CZ<br>B154:CZ2 | B23:O<br>B49:CG<br>B70:N<br>B176:O<br>B178:N<br>B241:ND2 | A142:O<br>A146:C<br>B20:ND2<br>B31:CE2<br>B52:CE1<br>B66:C<br>B71:CD<br>B173:CE<br>B175:CG2 |
| C21 | B24:CE2<br>B56:CD2 | A143:CE<br>B22:CB<br>B57:CZ<br>B67:CB<br>B68:N<br>B69:N | A147:CD1<br>B1:OG<br>B49:CG<br>B56:CG<br>B154:CZ2<br>B177:CG2 | B20:ND2<br>B23:N<br>B66:C<br>B178:O | B21:C<br>B31:CE2<br>B52:CE1<br>B70:N<br>B176:O<br>B179:CD1<br>B241:ND2 |
| C22 | B22:CB<br>B24:CE2<br>B57:CZ | B1:OG<br>B56:CD2<br>B67:O<br>B68:CA | A143:C<br>A147:C<br>B49:CG | B20:ND2<br>B21:C<br>B23:O<br>B31:CE2<br>B66:C<br>B69:CB<br>B154:CZ2<br>B177:CG2 | B2:O<br>B32:CG2<br>B52:CE1<br>B178:O<br>B41:ND2<br>B478:OE1 |
| C23 | B1:OG<br>B22:CB<br>B24:CD2 | B23:N<br>B57:CZ<br>B67:O<br>B68:CA<br>B69:N | A147:CE1<br>B49:CG<br>B56:CD2 | A143:CE<br>B20:ND2<br>B21:C<br>B31:CE2<br>B241:ND2 | A146:CZ<br>B2:N<br>B32:CG2<br>B56:CB<br>B154:CZ2<br>B177:CG2<br>B478:OE1 |

TABLE 2-continued

Environment of the phenylacetyl moiety in Penicillin G Acylase complexed with PenG

| PenG atoms | Atoms in the acylase within a certain distance range from PenG. Only closest atoms given. Distances in Å. Atom indication: chain-residue number:atom | | | | |
|---|---|---|---|---|---|
| (FIG. 3) | 3–4 | 4–5 | 5–6 | 6–7 | 7–8 |
|  |  |  |  |  | B477:OG1 |

TABLE 3

Environment of the 6-APA moiety in Penicillin G acylase complexed with PenG

| PenG atoms | Atoms in the acylase within a certain distance range from 6-APA moiety PenG. Only closest atoms given. Distances in Å. Atom indication: chain-residue number:atom | | | | |
|---|---|---|---|---|---|
| (FIG. 3) | 3–4 | 4–5 | 5–6 | 6–7 | 7–8 |
| S1 | A147:CE2 | B23:O | A146:NE B24:CA | B1:OG B25:N B69:CB B241:OD1 B256:CZ2 B381:CA B382:N | B380:C B455:CG |
| C2 |  | A147:CE2 B23:O | B381:CA | A146:NE B24:N B25:N B241:OD1 B256:NE1 B380:C B382:CA | B1:N B69:CB B261:CZ B379:OD1 B383:N B384:ND2 |
| C3 |  | B256:CZ2 B382:OG | A147:CE2 B23:O B241:OD1 | B1:N B241:CG B261:CZ B381:CA B384:ND2 | A146:NE B24:N B25:N B69:CB B256:CG B379:OD1 B380:O B383:N |
| N4 |  | A147:CE2 B241:OD1 B256:CZ2 | B23:O B69:CB B382:OG | B1:N B71:CG B261:CZ B384:ND2 | B24:N B381:CA |
| C5 | A147:CE2 | B69:CB | B23:O B241:OD1 B256:CZ2 | A146:O B1:OG B24:CA B71:CG B256:CE2 B382:OG | A150:CG2 B25:N B261:CZ B381:CA |
| C6 | A147:CE2 | B1:OG B23:O B69:CB B241:OD1 | B256:CZ2 | B24:N B68:C B71:CG B261:CZ B382:OGB | B2:N B22:C B70:N B240:C B241:N B384:ND2 |
| C7 | B241:OD1 | A147:CE2 B1:N B256:CZ2 B382:OG | B23:O B69:CB B261:CZ | B71:CG B240:O | B2:N B24:N B68:C B254:CE1 B381:CA B384:CG |
| O8 | B1:OD1 B241:OD1 B382:OG | B23:O B256:CZ2 B261:CZ | A147:CE2 B240:NE1 B382:ND2 | B69:CB B241:CA B381:C | B2:N B22:C B24:N B71:CG B383:O B390:NZ |
| C9 | B23:O N382:N | B381:CA | A147:CE2 B24:CA B25:N | A146:CZ B1:OG B241:OD1 | B22:C B26:CZ3 B27:OH |

TABLE 3-continued

Environment of the 6-APA moiety in Penicillin G acylase complexed with PenG

| PenG atoms | Atoms in the acylase within a certain distance range from 6-APA moiety PenG. Only closest atoms given. Distances in Å. Atom indication: chain-residue number:atom | | | | |
|---|---|---|---|---|---|
| (FIG. 3) | 3–4 | 4–5 | 5–6 | 6–7 | 7–8 |
|  |  |  |  | B380:O B383:N | B379:OD1 | B256:CZ2 B261:CZ B384:ND2 B477:OG1 |
| C10 |  |  | A147:CE2 B23:O B380:O B381:CA | A146:CZ B24:C B25:N B379:OD1 B380:C B381:O B382:OG | B256:NE1 |
| C11 |  |  | B256:NE1 | B382:OG A147:CE2 B241:OD1 B384:ND2 | A150:CG2 B23:O B69:CB B71:CG B261:CZ B381:CA |
| O12 |  |  | B256:NE1 | A147:CE2 | A150:CG2 A146:O B23:O B69:CB B71:CG B241:OD1 B382:OG B384:ND2 |
| O13 |  |  | B256:NE1 | B382:OG B384:ND2 | A147:CE2 B241:OD2 B255:CD1 B256:CE3 B379:OD1 B381:CA B383:N B384:N |

Example 2
Construction of the Mutagenesis/expression Vector for Vcylase

Figure 5:
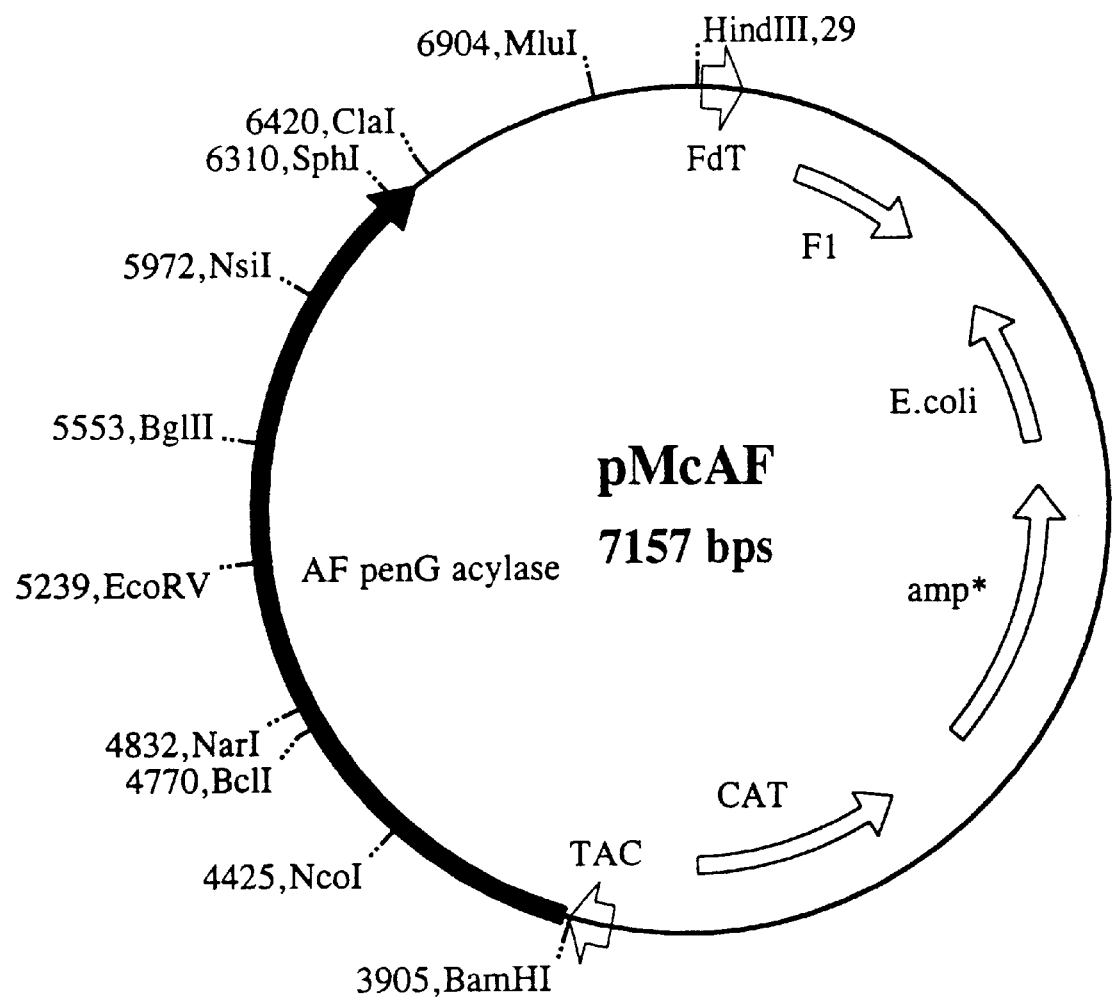
FIG. 5: pMcAF mutagenesis vector with *A. faecalis* Penicillin acylase gene, *E. coli* ori 'high' copy, Tac promotor, Fd-termintor, cap⁻, amp$^8$ f1-origin.

As starting material for the construction of a combined mutagenesis/expression vector the already described plasmid pMcTAFNde was used (EP-453048). This vector, which was constructed from pMcTNde and pAF1, harbors the complete penicillin acylase gene from *Alcaligenes faecalis*. In order to facilitate the construction of convenient gapped duplex molecules and to facilitate the exchange of PCR overlap extension fragments three new unique restriction sites were inserted without altering the coding information: EcoRV (position 5239), Nsi1 (pas. 5972) and Cla1 (pos. 6420). The resulting vector, pMcAF, which is shown in FIG. 5, was used to construct mutant acylase genes. The mutant acylases were produced in *E. coli* WK6 or HB101 laqI$^q$ under guidance of the tac promoter provided.

Example 3
Mutagenesis of *A. faecalis* acylase

At selected positions amino acid mutations were generated using lo the PCR overlap extension method described before. The amino acid positions in the respective subunit (A or B) are shown in table 4. The oligonucleotides used for the construction are also shown. Note that at position A143 and B67, B68, B69 an oligo with randomized codons was used.

Example 4
Assay of site directed mutants of penicillin acylase for correct folding and post translational processing using suitable auxotrophs of *E. coli*

*E. coli* HB101 laqI$^q$ cells harbouring the identified mutant acylase genes were tested on agar plates containing selective media.

Selective media for phenylacetyl L-leucine ('fal' ) were prepared as described by Garcia (supra). Minimal plates are as follows: M9 minimal agar, 1 mg/l thiamine, 10 mg/l L-proline, 0.2 mM IPTG and the appropriate antibiotic (50 μg/ml chloramphenicol (cap) or 75 μg/ml ampicillin (amp)). The available data from literature on expression of penicillin acylase indicate that proper folding and posttranslational processing of the chain are critical factors for obtaining catalytical viable penicillin acylase. In order to establish whether the mutant penicillin acylase is expressed properly as an active acylase 200 μg/ml of an acyl L-leucine was included into minimal plates. Transformants or mutants of *E. coli* HB101 (Leu) growing exclusively in the presence of the phenyl-acetyl-L-leucine are considered to harbour an active properly expressed penicillin acylase gene. Table 5 shows the result for several selected mutants.

In addition this method may be employed for an inital rough screening for acylases with an altered specificity. For selections on side-chain specificity of acylases 200 μg/ml of a desired acyl L-leucine was included into minimal plates. In case the acyl moiety is not recognized by the wild type penicillin acylase transformants or mutants of *E. coli* HB101 (Leu) growing exclusively in the presence of the desired acyl L-leucine are considered to harbour an acylase gene with the desired specificity (e.g. glutaryl-L-leucine). Examples of such selective substrates are a-D-aminoadipyl leucine, adipyl-leucine and glutaryl leucine. These compounds were purchased from LGSS, Transferbureau Nijmegen, The Netherlands.

TABLE 4

Synthetic DNA-oligonucleotides for PCR mutation.
(X = all possible amino acids)
(R = A or G; Y = C or T; S = C or G; W = A or T; B = C, G or T;
V = A, C, G; N = A, C, G or T)

| A.A.-position | A.A.-mutation | DNA-oligonucleotides: 5'-3' | |
|---|---|---|---|
| A143 | M: R, K | 5' GGGTGGGCTCCARGGCCAATCG 3' | [SEQ ID NO:1] |
|  |  | 5' GCGATTGGCCYTGGAGCCCAC 3' | [SEQ ID NO:2] |
| A147 | F: Y, h | 5' TGGGCTCCATGGCCAATCGCYACTCCGACACGAA 3' | [SEQ ID NO:3] |
|  | F: W | 5' TGGGCTCCATGGCCAATCGCTGGTCCGACACGAA 3' | [SEQ ID NO:4] |
| B24 | F:R, K | 5' CGGCCCACAGARGGGCTGGTACA ' | [SEQ ID NO:5] |
|  |  | 5' GTACCAGCCCYTCTGTGGGCC 3' | [SEQ ID NO:6] |
| B56 | L: R, K | 5' TCCGATCGTAARGTTTGGCACC 3' | [SEQ ID NO:7] |
|  |  | 5' GGTGCCAAACYTTACGATCGGAT 3' | [SEQ ID NO:8] |
|  | L: H | 5' TCCGATCGTACATTTTGGCACC 3' | [SEQ ID NO:9] |
|  |  | 5' GGTGCCAAAATGTACGATCGGAT 3' | [SEQ ID NO:10] |
|  | L: G, A, V | 5' CCGATCGTAGBCTTTGGCAC 3' | [SEQ ID NO:11] |
|  |  | 5' GTGCCAAAGVCTACGATCGG 3' | [SEQ ID NO:12] |
| B71 | P: F, Y | 5' GCTGGCTWCCAAGATGTGGTG 3' | [SEQ ID NO:13] |
|  |  | 5' ATCTTGGWAGCCAGCAGTCGC 3' | [SEQ ID NO:14] |
| B177 | I:R, K | 5' GATGGCGATATCCARGAACTGGTACTA 3' | [SEQ ID NO:15] |
|  | I: H | 5' GATGGCGATATCCCACAACTGGTACTA 3' | [SEQ ID NO:16] |
|  | I: C, M | 5' CAGCAAGATGGCGATATCCRTGAACTGGTACTACGC 3' | [SEQ ID NO:17] |
|  | I: S, T | 5' CAGCAAGATGGCGATATCCASCAACTGGTACTACGC 3' | [SEQ ID NO:18] |
| A143 | M: X | 5' GGGTGGGCTCCNNSGCCAATCGCTTCTC 3' | [SEQ ID NO:19] |
|  |  | 5' AAGCGATTGGCSNNGGAGCCCACCCAG 3' | [SEQ ID NO:20] |
| B67 | A: S, G, T | 5' GGGR/SCACTGCTGGGCCTCAAG 3' | [SEQ ID NO:21] |
|  |  | 5' AGTGS/YCCCCAGGCAATCTC 3' | [SEQ ID NO:22] |
|  | A: S, G | 5' GCCTGGGGRCACTGCTGGCCCGCAAG 3' | [SEQ ID NO:23] |
|  |  | 5' GCCAGCAGTGCYCCCCCAGGCAATCTC 3' | [SEQ ID NO:24] |

TABLE 4-continued

Synthetic DNA-oligonucleotides for PCR mutation.
(X = all possible amino acids)
(R = A or G; Y = C or T; S = C or G; W = A or T; B = C, G or T;
V = A, C, G; N = A, C, G or T)

| A.A.-position | A.A.-mutation | DNA-oligonucleotides: 5'-3' | |
|---|---|---|---|
| B67 | A: X | 5' CGAGATTGCCTGGGGGNNSNNSNNSGGCCCGCAAGATGTGGTGGAC 3' | [SEQ ID NO:25] |
| B68 | T: X | 5' CCACATCTTGCGGGCCSNNSNNSNNCCCCCAGGCAATCTCGC 3' | [SEQ ID NO:26] |
| B69 | A: X | | |

0

When wild type has low activity for an acyl group, mutants with increased activety can be picked up with this method by comparing the size of the halo produced by the mutant with respect to wild type. Useful side chains are phenoxyacetyl, p-hydroxyphenylglycyl, phenylglycyl.

TABLE 5

In vivo specifity of mutant acylsases. A and B in the first column refers to α and β subunit. ++ growth rate comparable to wild type; + growth rate reduce with respect to wild type; − no growth during 3 weeks.

| mutant | fenyl-acetyl-L-leucine |
|---|---|
| A:M143R | + |
| A:M143K | + |
| A:F147Y | ++ |
| A:F147H | ++ |
| A:F147W | ++ |
| B:F24R | − |
| B:F24K | ++ |
| B:L56R | |
| B:L56K | ++ |
| B:L56H | |
| B:I177R | |
| B:I177K | ++ |
| B:I177H | ++ |

Instead of leucine also the amino acid moiety of the selective substrate can be varied. In such case a suitable auxotrophic mutant of E. coli was used for selection. Instead also amide of the acyl moiety are useful componds for selection. Side-chain amide (e.g. phanylacetylamide, glutarylamide, adipylamide, α-aminoadipylamide) was added to a final concentration of 15 mM to minimal M9 medium supplemented with 0.2% of either succinate, glycerol or glucose as carbon source, and thiamine (1 μmg/ml), L-proline (10 μg/ml), 0.2 mM IPTG and the appropriate antibiotic.

All ammonium salts in the basal medium were replaced by the corresponding salts containing either $Na^+$ or $K^+$ ions in order to ensure selective growth on the amide. Amides with the desired side-chains were purchased from commercial suppliers or prepared according to standard techniques. E. coli strains JM101, WK6 and HB101 were used as hosts to select for mutant genes with specificity for the selective amides.

Example 5
Assay on targeted random mutants of Penicillin Acylase

In case of TRM mutagenesis a pool of mutants was plated on selective plates prior to DNA sequencing. Only the colonies which showed growth on one ore more of the selective media were characterized. The result for 2 TRM mutagenesis experiments are shown in table 6.

TABLE 6

In vivo specificity of mutant acylases. A in the first column refers to the α subunit. ++ growth rate comparable to wild type; + growth rate reduce with respect to wild type; − no growth during 3 weeks.

| mutant | fenyl-acetyl-l-leucine |
|---|---|
| A:M143C | ++ |
| A:M143G | + |
| A:M143D | + |
| A:M143T | ++ |
| A:M143V | ++ |
| A:M143L | ++ |

Example 6
Increased Specific Activity and Altered Specificity

The catalytic parameters of A.faecalis PenG acylase mutants were determined for different substrates. The altered specificities for the mutants are exemplified in Tables 7 and 8. Compared to wild type the mutants A:M143V and B:L56K exhibit a higher turn-over rate for the deacylation of PenV and CefG. A:F147Y is more active compared to wild type when used in the deamidation of D-phenylglycinamide.

Figure 6:
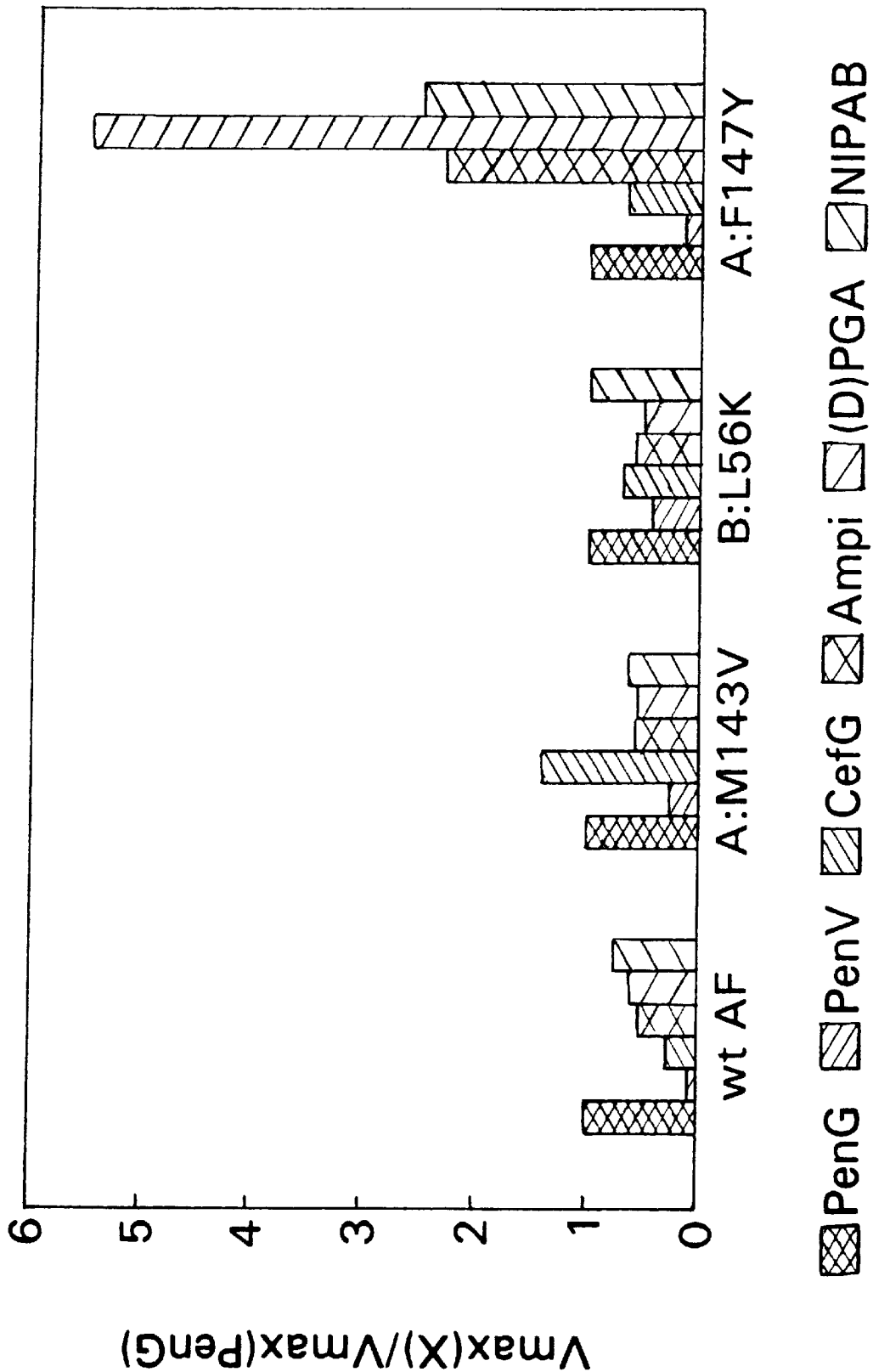
FIG. 6: Maximal deacylation velocity of wild type A. faecalis acylase and the mutants B:L56G, B:L56A, B:L56V, B:I177V, B:I177S, B:A67S, B:A67G for various substrates. Velocities for each variant are relative to PenG: $V_{sax}(X)/V_{sax}(PenG)$. X represents PenV, CefG, Ampicillin (Ampi), (D)Phenylglycinamide ((D)PGA) or NIPAB.
Figure 7:
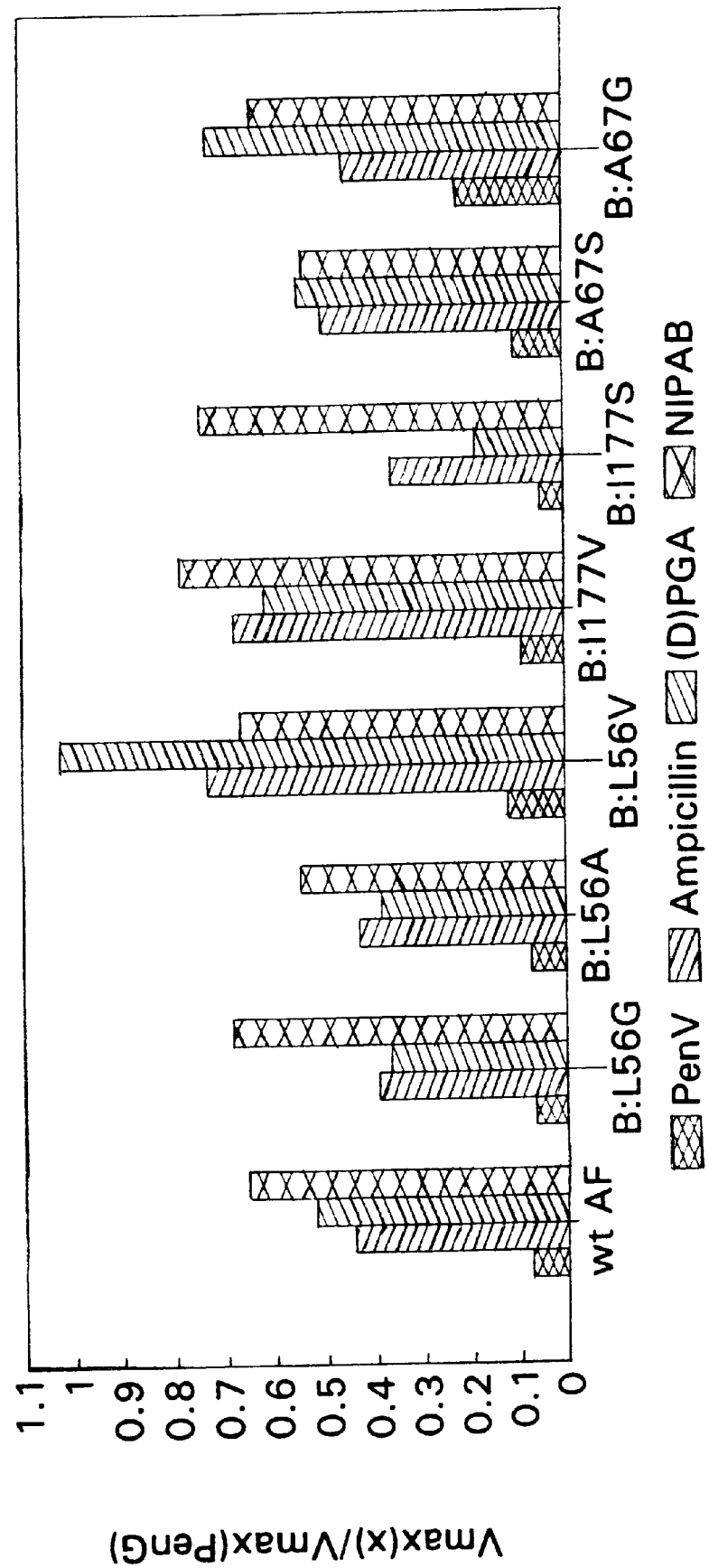
FIG. 7: The maximal deacylation velocity of wild type *A. faecalis* acylase and the mutants A:M143V, B:L56K, A:F147Y for various substrates. Velocities for each variant are relative to PenG: $V_{sax}(X)/V_{sax}(PenG)$. X represents PenV, CefG, Ampicillin (Ampi), (D)Phenylglycinamide ((D)PGA) or NIPAB.

At high substrate concentrations, which is usually the situation in many industrial conversion processes, the acylase will be completely saturated with substrate and as a consequence the conversion will proceed at maximal velocity. In FIG. 6 the maximal velocity for a number of substrates is plotted for the wild type A. faecalis acylase and for some mutants. Velocities are scaled relative to PenG whereby $V_{sax}$ for PenG has been set to 1. Wild type PenG acylase shows the highest activity for PenG as was expected. However the substitution A:M143V turns the enzyme into a CefG acylase, while the substitution A:F147Y turns the enzyme into a powerful amidase for the deamidation of D-Phenylglycinamide ((D)PGA). In addition the deacylation velocities of A:F147Y are higher for ampicillin and NIPAB than for PenG. In FIG. 7 the $V_{sax}$ value which was measured for mutants B:L56G, B:L56A, B: L56V, B:177V, BI177S, B:A67S, B:A67G for the given substrates is compared to the $V_{sax}$ for PenG in a similar way as was done in FIG. 6. Specificity has shifted with respect to wild type. E.g. mutant B:1l77S exhibits a reduced deacylation rate on ampicilin and an improved activiry on D-phenylglycinamide ((D)PGA).

In general the specificity or selectivity of an enzyme in the sense of discrimination between two competing substrates is determined by comparing the $V_{sax}/K_s$ (or $k_{cat}/K_s$) of the two substrates. In table 9 this ratio has been compared for different substrate combinations. Especially the considerable increase of the specificity of the A:F147Y mutant for (D)PGA is striking.

TABLE 9

Selectivity of the wild type enzyme compared to selectivity of the mutants for a number of substrates.

| $(V_{max}/K_s)_{s1}/$ $(V_{max}/K_s)_{s2}$ $(\times 100)$ | | wild | | | |
|---|---|---|---|---|---|
| S1 | S2 | type | A:M143V | B:L56K | A:F147Y |
| PenV | PenG | 0.97 | 4.93 | 1.21 | 1.10 |
| CefG | PenG | 54.95 | 119.33 | 7.00 | 44.44 |
| PenV | CefG | 1.76 | 4.13 | 17.35 | 2.48 |
| Ampi | PenG | 14.80 | 22.70 | 3.40 | 35.30 |
| (D)PGA | Ampi | 9.50 | 4.10 | 3.00 | 367.60 | tiomerically pure semisynthetic antibiotics from racemic mixtures of α-carbon substituted phenylacetyl side chains or activated derivatives of the α-carbon substituted phenylacetyl side chain (e.g. phenylglycine-amides or -esters, p-hydroxyphenylglycine-amides or -esters) which contain a chiral α-carbon due to the presence of an amino group (e.g. Ampicillin, Cefalexin, Amoxycillin, Cefadroxyl, Cephachlor) or a hydroxyl group (Cephamandol).

Table 10 shows that for phenylglycinamide wild type PenG acylases show a preference for the D enantiomer. For a racemic mixture (1:1) of D and L phenylglycineamide $v_{D/vL}$ equals $(V_{sax}/K_s)^{D-PGA}/(V_{sax}/K_s)^{L-PGA}$ where $v_D$ and $v_L$ represent velocities of deamidation of D and L enantiomer respectively. So for the wild type *A. faecalis* the velocity of deamidation of the D enantiomer is 5 times faster than for the L enantiomer. For mutant A:F143Y the steroselectivity which is expressed as $(V_{sax}/K_s)^{D-PGA}/(V_{sax}/K_s)^{L-PGA}$ has increased from 5.10 to 36.52. This means that the velocity of deamidation of D enantiomer is 36.52 times faster than that of L instead of only 5.10 times as for the wild

TABLE 7

Catalytic parameters $K_m$ and $V_{max}$ as were determined for wild type *Alcaligenes faecalis* PenG acylase and some mutants. Assay conditions: NIPAB, 0.1M NaH2PO4, pH 7.5, 25° C.; PenG and PenV, 40 mM NaH$_2$PO$_4$, pH 7.5, 37° C.; CefG, 20 mM NaH$_2$PO$_4$, pH 7.5, 37° C.; Amoxi(cillin), Ampi(cillin) and D-Phenylglycineamide ((D)PGA), 20 mM NaH$_2$PO$_4$, pH 7.0, 37° C.

| | wild type | | A:M143V | | B:L56K | | A:F147Y | |
|---|---|---|---|---|---|---|---|---|
| | $K_m$ ($\mu$M) | $V_{max}$ (U/mg) | $K_m$ ($\mu$M) | $V_{max}$ (U/mg) | $K_m$ ($\mu$M) | $V_{max}$ (U/mg) | $K_m$ ($\mu$M) | $V_{max}$ (U/mg) |
| NIPAB | 4 | 37.0 | 17 | 35.7 | 28 | 47.3 | 5 | 18.0 |
| PenG | 2 | 45.5 | 6 | 40.5 | 1 | 36.4 | 4 | 5.9 |
| PenV | 18 | 4.0 | 31 | 10.3 | 35 | 15.5 | 51 | 0.8 |
| CefG | 1 | 12.5 | 7 | 56.4 | 10 | 25.5 | 6 | 4.0 |
| Ampi | 700 | 23.5 | 1500 | 23.0 | 1700 | 20.9 | 2600 | 13.6 |
| (D)PGA | 8600 | 27.5 | 35000 | 22.2 | 49000 | 18.2 | 1700 | 32.7 |
| Amoxi | 14000 | .9 | 21000 | .2 | | | 19000 | 0.1 |

TABLE 8

Catalytic parameters $K_s$ and $V_{max}$ as were determined for wild type *Alcaligenes fascalis* PenG acylase and some mutants. Assay conditions: NIPAB, 0.1 M NaH2PO$_4$, pH 7.5, 25° C. For mutants B:A678 and B:A67G $V_{max}$ in U/ml.

| | $K_s$ ($\mu$M) | $V_{max}$ (U/mg) | $V_{max}/K_s$ |
|---|---|---|---|
| wt AF | 4 | 37.0 | 9.3 |
| B:L56G | 12 | 21.3 | 1.8 |
| B:L56A | 14 | 37.1 | 2.7 |
| B:L56V | 9 | 28.2 | 3.1 |
| B:I177V | 10 | 34.5 | 3.5 |
| B:I177S | 76 | 30.2 | 0.4 |
| B:A67S | 5 | 7.1 | |
| B:A67G | 11 | 1.1 | |

Example 7
Improved Stereospecificity of PenG Acylase.

Wild type A.faecalis and *E. coli* PenG acylase show a preference for the D enantiomer of penicillins with an α-carbon substituted side chain. Examples are ampicillin, cefalexin, amoxicillin, cefadroxyl, and cefaclor. An increased stereospecifity of Penicillin G acylases is desired in order to obtain Penicillin G acylase which shows an improved enantiomeric excess in conversions with racemic mixtures of chiral compounds. Such property makes the Penicillin G acylase extremely useful for synthesis of enantype.

TABLE 10

Stereospecificity of the wild type enzymes *A. faecalis* and *E. coli* versus stereospecificity of the mutants for DL-phenylglycinamide (PGA). Assay conditions DL phenylglycineanide (PGA): 20 mM NaH$_2$PO$_4$, pH 7.0, 37° C.

| | $(V_{max}/K_s)^{D-PGA}/(V_{max}/K_s)^{L-PGA}$ |
|---|---|
| Wild type *E. coli* | 3.32 |
| Wild type *A. faecalis* | 5.10 |
| A:M143V | 5.70 |
| B:L56K | 3.25 |
| A:F147Y | 36.52 |

Example 8
Reduced product Inhibition.

The complete conversion of NIPAB was followed as a funtion of time at 20, 50 and 100 $\mu$M NIPAB by following the increase in absorbtion at 405 nm. Products of this conversion are phenylacetic acid and 3-amino-6-nitrobenzoic acid. The conversion was performed at 25° C. in 0.1 M NaH$_2$PO$_4$.H$_2$O buffer pH 7.5. The progress curves of the deacylation of NIPAB could be fitted very well when product inhibition by phenylacetic acid was taken into account. The dissociation constants (usually referred to as inhibition constant K$_i$) for phenylacetic acid which could be derived from the progress curves is shown in table 11. The benefits of some mutants which are less sensitive to product inhibition are shown in table 12. For these mutants the yield of the conversion in a fixed time span is higher than for wild type. Alternatively, in order to obtain a certain yield a shorter conversion time is needed for the mutants.

The conversion of PenG is usually performed at concentrations as high as 200 mM. Using an identical amount of PenG units, the mutant A:M143V may reach in 20 minutes a conversion yield of 90% while wild type approaches 84% in this time span.

TABLE 11

Inhibition of PenG acylase by phenylacetic acid (PA). $K_i$ (inhibition constant PA) represents the dissociation constant. The catalytic parameters were determined at 25° C. in 0.1 M $NaH_2PO_4.H_2O$ buffer pH 7.5.

|  | $K_i^{Phenylacetic\ acid}(\mu M)$ |
|---|---|
| wt AF | 11 |
| B:L56K | 115 |
| B:L56V | 31 |
| B:L56A | 59 |
| B:L56G | 55 |
| B:A67G | 65 |
| B:I177S | 252 |
| B:I177V | 35 |
| A:M143V | 74 |

TABLE 12

Progress of the NIPAB conversion in time. The yield represents the fraction of substrate which has been converted. Conversion of 200 μM NIPAB, 25° C. in 0.1 M $NaH_2PO_4.H_2O$ buffer pH 7.5 using 0.1 Unit of enzyme (NIPAB units).

|  | Yield (%) 15 min | Yield (%) 30 min |
|---|---|---|
| wt AF | 61.8 | 91.8 |
| B:L56A | 61.3 | 93.3 |
| B:L56G | 62.3 | 94.5 |
| B:A67G | 63.8 | 96.4 |
| A:M143V | 60.5 | 92.7 |

Example 9

Altered molar ratio aminolysis/hydrolysis. The synthesis of ampicillin from (D)phenylglycinamide(D-PGA) and 6APA using PenG acylases. To a buffered solution containing (D)phenylglycinamide(D-PGA) and 6APA PenG acylase wild type or mutants were added. At different time intervals samples were analyzed and the composition of the samples was determined according to the methods described in the experimental section. The results are shown in tables 13 and 14. Some mutants show improved molar ratio aminolysis/hydrolysis.

TABLE 13

Molar ratio aminolysis or synthesis versus hydrolysis (S/H) obtained in the synthesis of ampicillin by PenG acylases. Initial concentrations 12.4 mM D-PGA and 62 mM ampicillin. Experimental conditions: 0.1 M Tris buffer pH 7.8, temperature 4° C., enzymes dosed at 0.7 NIPAB units per ml.

| | Aminolysis/Hydrolysis molar ratio: Ampicillin/D-Phenylglycine | | | |
|---|---|---|---|---|
|  | t = 5 min | t = 15 min | t = 30 min | t = 60 min |
| wt AF | 0.95 | 0.92 | 0.69 | 0.36 |
| A:M143V | 0.75 | 0.92 | 0.94 | 0.71 |
| B:L56G | 0.78 | 1.03 | 1.02 | 0.79 |
| B:I177S | 0.30 | 0.79 | 1.05 | 1.17 |

TABLE 14

Molar ratio aminolysis or synthesis over hydrolysis (S/H) obtained in the synthesis of ampicillin by PenG acylases. Initial concentrations 10 mM D-PGA and 30 mM ampicillin. Experimental condition: 0.1 M Tris buffer pH 7.8, temperature 25° C., enzymes dosed at 1.4 D-PGA units per ml.

| | Aminolysis/Hydrolysis molar ratio: Ampicillin/D-Phenylglycine | | |
|---|---|---|---|
|  | t = 10 min | t = 30 min | t = 60 min |
| wt AF | 0.43 | 0.20 | 0.06 |
| A: M143V | 0.50 | 0.31 | 0.15 |

We claim:

1. An isolated mutant prokaryotic Penicillin G acylase or its preenzmye or preproenzyme having:
    an amino acid substitution at one or more of the positions corresponding to A139 to A142 and A148 to A152 as set forth in SEQ ID NO: 27, B20 to B27, B31, B49 to B52, B56, B57, B65, B67 to B72, B154 to B157, B173 to B179, B239 to B241, B250 to B263, B379 to B387, B390, B455, B474 to B480 as set forth in SEQ ID NO:32 in *Alcaligenes faecalis* Penicillin G acylase or its pre- or preproenzyme, wherein the substitution at position A141 results in a substituent amino acid selected from the group consisting of Ala, Arg, Asn, Cys, Gln, Glu, Gly, His, Ile, Leu, Lys, Met, Phe, Pro, Ser, Thr, Trp, Tyr, and Val; and
    an altered substrate specificity or altered specific activity relative to the corresponding wild-type unsubstituted Penicillin G acylase.

2. A mutant acylase according to claim 1, wherein said acylase is obtained from a member of the group consisting of *Escherichia coli, Kluyvera citrophila, Providencia rettgeri, Arthrobacter viscosis,* and *Alcaligenes faecalis.*

3. A mutant acylase according to claim 1, wherein the amino acid substitution is one of the following:
    A141 (Gly) as set forth in SEQ ID NO: 27 to Cys, Thr, Met, Ala, Val, or Leu.

4. A mutant acylase according to claim 1, wherein the amino acid substitution is one of the following:
    B24 (Phe) as set forth in SEQ ID NO: 32 to Ala, Leu or any other amino acid.

5. An isolated mutant prokaryotic Penicillin G acylase or its preenzyme or preproenzyme having an amino acid substitution at a position corresponding to A141 (Gly) as set forth in SEQ ID NO: 27 wherein A141 (Gly) is changed to Cys, Thr, Met, Ala, Val or Leu.

6. An isolated mutant prokaryotic Penicillin G acylase or its preenzyme or preproenzyme having an amino acid substitution at a position corresponding to B24 (Phe) as set forth in SEQ ID NO: 32 wherein B24 (Phe) is changed to Ala or Leu.

7. A nucleic acid sequence encoding a mutant acylase as defined in claim 1.

8. An expression vector comprising a nucleic acid sequence as defined in claim 7 operably linked to a promoter sequence capable of directing its expression in a host cell.

9. A microorganism transformed with an expression vector as defined in claim 8.

10. A mic roorganism according to claim 9, which is a microorganism of the genus Cephalosoprium or the genus Penicillium.

11. A process of preparing an isolated mutant acylase as defined in claim 1, which process comprises:

culturing a microorganism as defined in claim 9, whereby said mutant acylase is produced; and isolating said acylase.

12. A method for deacylating a 6-acylated penicillanic acid, a 7-acylated (desacetoxy) cephalosporanic acid or a salt or ester thereof to form the corresponding 6-amino penicillanic acid or 7-amino (desacetoxy) cephalosporanic acid or salt or ester thereof, respectively, which comprises contacting said 6-acylated or 7-acylated compound with a mutant acylase as defined in claim 1 under conditions suitable for deacylation to occur.

13. A method for producing a semi-synthetic 6-acylated penicillanic acid, a 7-acylated (desacetoxy) cephalosporanic acid or a salt or ester thereof which comprises contacting a corresponding 6-amino or 7-amino β-lactam or salt or ester thereof, respectively, and an acylating agent with a mutant acylase as defined in claim 1 under conditions suitable for acylation to occur.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: other nucleic acid

```
    (xi) SEQUENCE DESCRIPTION: SEQ ID NO:1:

GGGTGGGCTC CARGGCCAAT CG                                             22

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

GCGATTGGCC YTGGAGCCCA C                                              21

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

TGGGCTCCAT GGCCAATCGC YACTCCGACA CGAA                                34

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

TGGGCTCCAT GGCCAATCGC TGGTCCGACA CGAA                                34

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

CGGCCCACAG ARGGGCTGGT ACA                                            23

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

GTACCAGCCC YTCTGTGGGC C                                              21
```

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

TCCGATCGTA ARGTTTGGCA CC                                    22

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

GGTGCCAAAC YTTACGATCG GAT                                 23

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

TCCGATCGTA CATTTTGGCA CC                                   22

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

GGTGCCAAAA TGTACGATCG GAT                                 23

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

CCGATCGTAG BCTTTGGCAC                                     20

(2) INFORMATION FOR SEQ ID NO:12:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

GTGCCAAAGV CTACGATCGG                                                    20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

GCTGGCTWCC AAGATGTGGT G                                                  21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

ATCTTGGWAG CCAGCAGTCG C                                                  21

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

GATGGCGATA TCCARGAACT GGTACTA                                            27

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

GATGGCGATA TCCCACAACT GGTACTA                                            27

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

CAGCAAGATG GCGATATCCR TGAACTGGTA CTACGC                                36

(2) INFORMATION FOR SEQ ID NO:18:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:18:

CAGCAAGATG GCGATATCCA SCAACTGGTA CTACGC                                36

(2) INFORMATION FOR SEQ ID NO:19:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:19:

GGGTGGGCTC CNNSGCCAAT CGCTTCTC                                          28

(2) INFORMATION FOR SEQ ID NO:20:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:20:

AAGCGATTGG CSNNGGAGCC CACCCAG                                           27

(2) INFORMATION FOR SEQ ID NO:21:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:21:

GGGVCACTGC TGGGCCTCAA G                                                 21

(2) INFORMATION FOR SEQ ID NO:22:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:22:

```
AGTGBCCCCC AGGCAATCTC                                                    20
```

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

```
GCCTGGGGGR CACTGCTGGC CCGCAAG                                            27
```

(2) INFORMATION FOR SEQ ID NO:24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:24:

```
GCCAGCAGTG CYCCCCCAGG CAATCTC                                            27
```

(2) INFORMATION FOR SEQ ID NO:25:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:25:

```
CGAGATTGCC TGGGGGNNSN NSNNSGGCCC GCAAGATGTG GTGGAC                       46
```

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:26:

```
CCACATCTTG CGGGCCSNNS NNSNNCCCCC AGGCAATCTC GC                           42
```

(2) INFORMATION FOR SEQ ID NO:27:

(i) SEQUENCE CHARACTERISTICS:
        (A) LENGTH: 202 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

```
Gln Val Gln Ser Val Glu Val Met Arg Asp Ser Tyr Gly Val Pro His
1               5                   10                  15
```

```
Val Phe Ala Asp Ser His Tyr Gly Leu Tyr Tyr Gly Tyr Gly Tyr Ala
             20                  25                  30

Val Ala Gln Asp Arg Leu Phe Gln Met Asp Met Ala Arg Arg Ser Phe
         35                  40                  45

Val Gly Thr Thr Ala Ala Val Leu Gly Pro Gly Glu Gln Asp Ala Tyr
 50                      55                  60

Val Lys Tyr Asp Met Gln Val Arg Gln Asn Phe Thr Pro Ala Ser Ile
 65                  70                  75                  80

Gln Arg Gln Ile Ala Ala Leu Ser Lys Asp Glu Arg Asp Ile Phe Arg
                     85                  90                  95

Gly Tyr Ala Asp Gly Tyr Asn Ala Tyr Leu Glu Gln Val Arg Arg Arg
                100                 105                 110

Pro Glu Leu Leu Pro Lys Glu Tyr Val Asp Phe Asp Phe Gln Pro Glu
            115                 120                 125

Pro Leu Thr Asp Phe Asp Val Val Met Ile Trp Val Gly Ser Met Ala
        130                 135                 140

Asn Arg Phe Ser Asp Thr Asn Leu Glu Val Thr Ala Leu Ala Met Arg
145                 150                 155                 160

Gln Ser Leu Glu Lys Gln His Gly Pro Glu Arg Gly Arg Ala Leu Phe
                165                 170                 175

Asp Glu Leu Leu Trp Ile Asn Asp Thr Thr Ala Pro Thr Thr Val Pro
            180                 185                 190

Ala Pro Ala Ala Glu His Lys Pro Gln Ala
        195                 200

(2) INFORMATION FOR SEQ ID NO:28:

(i) SEQUENCE CHARACTERISTICS:
        (A) LENGTH: 209 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Glu Gln Ser Ser Ser Glu Ile Lys Ile Val Arg Asp Glu Tyr Gly Met
 1               5                  10                  15

Pro His Ile Tyr Ala Asn Asp Thr Trp His Leu Phe Tyr Gly Tyr Gly
             20                  25                  30

Tyr Val Val Ala Gln Asp Arg Leu Phe Gln Met Glu Met Ala Arg Arg
         35                  40                  45

Ser Thr Gln Gly Thr Val Ala Glu Val Leu Gly Lys Asp Phe Val Lys
 50                      55                  60

Phe Asp Lys Asp Ile Arg Arg Asn Tyr Trp Pro Asp Ala Ile Arg Ala
 65                  70                  75                  80

Gln Ile Ala Ala Leu Ser Pro Glu Asp Met Ser Ile Leu Gln Gly Tyr
                 85                  90                  95

Ala Asp Gly Met Asn Ala Trp Ile Asp Lys Val Asn Thr Asn Pro Glu
                100                 105                 110

Thr Leu Leu Pro Lys Gln Phe Asn Thr Phe Gly Phe Thr Pro Lys Arg
            115                 120                 125

Trp Glu Pro Phe Asp Val Ala Met Ile Phe Val Gly Thr Met Ala Asn
        130                 135                 140

Arg Phe Ser Asp Ser Thr Ser Glu Ile Asp Asn Leu Ala Leu Leu Thr
145                 150                 155                 160
```

```
Ala Leu Lys Asp Lys Tyr Gly Val Ser Gln Gly Met Ala Val Phe Asn
                165                 170                 175

Gln Leu Lys Trp Leu Val Asn Pro Ser Ala Pro Thr Thr Ile Ala Val
                180                 185                 190

Gln Glu Ser Asn Tyr Pro Leu Lys Phe Asn Gln Gln Asn Ser Gln Thr
                195                 200                 205

Ala
```

(2) INFORMATION FOR SEQ ID NO:29:

(i) SEQUENCE CHARACTERISTICS:
        (A) LENGTH: 209 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

```
Ala Ser Pro Pro Thr Glu Val Lys Ile Val Arg Asp Glu Tyr Gly Met
1               5                   10                  15

Pro His Ile Tyr Ala Asp Asp Thr Tyr Arg Leu Phe Tyr Gly Tyr Gly
                20                  25                  30

Tyr Val Val Ala Gln Asp Arg Leu Phe Gln Met Glu Met Ala Arg Arg
                35                  40                  45

Ser Thr Gln Gly Thr Val Ser Glu Val Leu Gly Lys Ala Phe Val Ser
50                  55                  60

Phe Asp Lys Asp Ile Arg Gln Asn Tyr Trp Pro Asp Ser Ile Arg Ala
65                  70                  75                  80

Gln Ile Ala Ser Leu Ser Ala Glu Asp Lys Ser Ile Leu Gln Gly Tyr
                85                  90                  95

Ala Asp Gly Met Asn Ala Trp Ile Asp Lys Val Asn Ala Ser Pro Asp
                100                 105                 110

Lys Leu Leu Pro Gln Gln Phe Ser Thr Phe Gly Phe Lys Pro Lys His
                115                 120                 125

Trp Glu Pro Phe Asp Val Ala Met Ile Phe Val Gly Thr Met Ala Asn
                130                 135                 140

Arg Phe Ser Asp Ser Thr Ser Glu Ile Asp Asn Leu Ala Leu Leu Thr
145                 150                 155                 160

Ala Val Lys Asp Lys Tyr Gly Asn Asp Glu Gly Met Ala Val Phe Asn
                165                 170                 175

Gln Leu Lys Trp Leu Val Asn Pro Ser Ala Pro Thr Thr Ile Ala Ala
                180                 185                 190

Arg Glu Ser Ser Tyr Pro Leu Lys Phe Asp Leu Gln Asn Thr Gln Thr
                195                 200                 205

Ala
```

(2) INFORMATION FOR SEQ ID NO:30:

(i) SEQUENCE CHARACTERISTICS:
        (A) LENGTH: 207 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

```
Ala Lys Asn Glu Gly Val Lys Val Val Arg Asp Asn Phe Gly Val Pro
```

```
1               5                    10                   15
His Leu Tyr Ala Lys Asn Lys Lys Asp Leu Tyr Glu Ala Tyr Gly Tyr
                20                  25                  30

Val Met Ala Lys Asp Arg Leu Phe Gln Leu Glu Met Phe Arg Arg Gly
                35                  40                  45

Asn Glu Gly Thr Val Ser Glu Ile Phe Gly Asp Tyr Leu Ser Lys
50                              55                  60

Asp Glu Gln Ser Arg Arg Asp Gly Tyr Ser Asn Lys Glu Ile Lys Lys
65                  70                  75                  80

Met Ile Asp Gly Leu Asp Arg Gln Pro Arg Glu Leu Ile Ala Lys Phe
                85                  90                  95

Ala Glu Gly Ile Ser Arg Tyr Val Asn Glu Ala Leu Lys Asp Pro Asp
                100                 105                 110

Asp Lys Leu Ser Lys Glu Phe His Glu Tyr Gln Phe Leu Pro Gln Lys
                115                 120                 125

Trp Thr Ser Thr Asp Val Val Arg Val Tyr Met Val Ser Met Thr Tyr
                130                 135                 140

Leu Trp Ile Ile Thr Arg Glu Leu Lys Asn Ala Glu Ile Leu Ala Lys
145                 150                 155                 160

Leu Glu His Glu Tyr Gly Thr Glu Val Ser Arg Lys Met Phe Asp Asp
                165                 170                 175

Leu Val Trp Lys Asn Asp Pro Ser Ala Pro Thr Ser Ile Val Ser Glu
                180                 185                 190

Gly Lys Pro Lys Arg Glu Ser Ser Ser Gln Ser Leu Gln Lys Leu
                195                 200                 205

(2) INFORMATION FOR SEQ ID NO:31:

(i) SEQUENCE CHARACTERISTICS:
        (A) LENGTH: 284 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Met Lys Lys His Leu Ile Ser Ile Ala Ile Val Leu Ser Leu Ser Ser
1               5                   10                  15

Leu Ser Leu Ser Ser Phe Ser Gln Ser Thr Gln Ile Lys Ile Glu Arg
                20                  25                  30

Asp Asn Tyr Gly Val Pro His Ile Tyr Ala Asn Asp Thr Tyr Ser Leu
                35                  40                  45

Phe Tyr Gly Tyr Gly Tyr Ala Val Ala Gln Asp Arg Leu Phe Gln Met
                50                  55                  60

Glu Met Ala Lys Arg Ser Thr Gln Gly Thr Val Ser Glu Val Phe Gly
65                  70                  75                  80

Lys Asp Tyr Ile Ser Phe Asp Lys Glu Ile Arg Asn Asn Tyr Trp Pro
                85                  90                  95

Asp Ser Ile His Lys Gln Ile Asn Gln Leu Pro Ser Gln Glu Gln Asp
                100                 105                 110

Ile Leu Arg Gly Tyr Ala Asp Gly Met Asn Ala Trp Ile Lys Gln Ile
                115                 120                 125

Asn Thr Lys Pro Asp Asp Leu Met Pro Lys Gln Phe Ile Asp Tyr Asp
                130                 135                 140

Phe Leu Pro Ser Gln Trp Thr Ser Phe Asp Val Ala Met Ile Met Val
```

```
145                 150                 155                 160
Gly Thr Met Ala Asn Arg Phe Ser Asp Met Asn Ser Glu Ile Asp Asn
                165                 170                 175

Leu Ala Leu Leu Thr Ala Leu Lys Asp Lys Tyr Gly Glu Gln Leu Gly
            180                 185                 190

Val Glu Phe Phe Asn Gln Ile Asn Trp Leu Asn Pro Asn Ala Pro
            195                 200                 205

Thr Thr Ile Ser Ser Glu Glu Phe Thr Tyr Ser Asp Ser Gln Lys Thr
            210                 215                 220

Lys Asn Ile Ser Gln Leu Asn Gln Ile Ser Asp Tyr Arg Leu Thr Ala
225                 230                 235                 240

Pro Met Phe Glu Arg Thr Ala Lys Asp Thr Thr Gly Lys Val Leu Ala
                245                 250                 255

Leu Ser Ser Gln Glu Asn Asn Ala Leu Ile Ala Lys Gln Tyr Glu Gln
            260                 265                 270

Ser Gly Ala Asn Gly Leu Ala Gly Tyr Pro Thr Thr
            275                 280
```

(2) INFORMATION FOR SEQ ID NO:32:

(i) SEQUENCE CHARACTERISTICS:
        (A) LENGTH: 551 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Ser Asn Leu Trp Ser Thr Arg Pro Glu Arg Val Gln Glu Gly Ser Thr
1               5                   10                  15

Val Leu Ile Asn Gly Pro Gln Phe Gly Trp Tyr Asn Pro Ala Tyr Thr
            20                  25                  30

Tyr Gly Ile Gly Leu His Gly Ala Gly Phe Asp Val Val Gly Asn Thr
            35                  40                  45

Pro Phe Ala Tyr Pro Ile Val Leu Phe Gly Thr Asn Ser Glu Ile Ala
        50                  55                  60

Trp Gly Ala Thr Ala Gly Pro Gln Asp Val Val Asp Ile Tyr Gln Glu
65                  70                  75                  80

Lys Leu Asn Pro Ser Arg Ala Asp Gln Tyr Trp Phe Asn Asn Ala Trp
                85                  90                  95

Arg Thr Met Glu Gln Arg Lys Glu Arg Ile Gln Val Arg Gly Gln Ala
            100                 105                 110

Asp Arg Glu Met Thr Ile Trp Arg Thr Val His Gly Pro Val Met Gln
            115                 120                 125

Phe Asp Tyr Asp Gln Gly Ala Ala Tyr Ser Lys Lys Arg Ser Trp Asp
        130                 135                 140

Gly Tyr Glu Val Gln Ser Leu Leu Ala Trp Leu Asn Val Ala Lys Ala
145                 150                 155                 160

Arg Asn Trp Thr Glu Phe Leu Asp Gln Ala Ser Lys Met Ala Ile Ser
                165                 170                 175

Ile Asn Trp Tyr Tyr Ala Asp Lys His Gly Asn Ile Gly Tyr Val Ser
            180                 185                 190

Pro Ala Phe Leu Pro Gln Arg Pro Ala Asp Gln Asp Ile Arg Val Pro
            195                 200                 205

Ala Lys Gly Asp Gly Ser Met Glu Trp Leu Gly Ile Lys Ser Phe Asp
```

-continued

```
            210                 215                 220
Ala Ile Pro Lys Ala Tyr Asn Pro Gln Gly Tyr Leu Val Asn Trp
225                 230                 235                 240

Asn Asn Lys Pro Ala Pro Asp Lys Thr Asn Thr Asp Thr Tyr Tyr Trp
                245                 250                 255

Thr Tyr Gly Asp Arg Met Asn Glu Leu Val Ser Gln Tyr Gln Gln Lys
                260                 265                 270

Asp Leu Phe Ser Val Gln Glu Ile Trp Glu Phe Asn Gln Lys Ala Ser
            275                 280                 285

Tyr Ser Asp Val Asn Trp Arg Tyr Phe Arg Pro His Leu Glu Lys Leu
        290                 295                 300

Ala Gln Gln Leu Pro Ala Asp Ser Ser Lys Ala Ala Leu Thr Met
305                 310                 315                 320

Leu Leu Ala Trp Asp Gly Met Glu Gln Asp Gln Gly Gly Gln Asn Ala
                325                 330                 335

Gly Pro Ala Arg Val Leu Phe Lys Thr Trp Leu Glu Glu Met Tyr Lys
                340                 345                 350

Gln Val Leu Met Pro Val Val Pro Glu Ser His Arg Ala Met Tyr Ser
            355                 360                 365

Gln Thr Gly Phe Ala Thr Gln Gln Gly Pro Asn Pro Gly Ser Ile Asn
        370                 375                 380

Leu Ser Met Gly Thr Lys Val Leu Leu Arg Ala Leu Val Leu Glu Ala
385                 390                 395                 400

His Pro Asp Pro Lys Arg Val Asn Val Phe Gly Glu Arg Ser Ser Gln
                405                 410                 415

Glu Ile Met His Thr Ala Leu Gln Asn Ala Gln Ala Arg Leu Ser Gln
                420                 425                 430

Glu Gln Gly Ala Gln Met Ala Arg Trp Thr Met Pro Thr Ser Val His
            435                 440                 445

Arg Phe Ser Asp Lys Asn Phe Thr Gly Thr Pro Gln Thr Met Pro Gly
        450                 455                 460

Asn Thr Phe Ala Phe Thr Gly Tyr Gln Asn Arg Gly Thr Glu Asn Asn
465                 470                 475                 480

Arg Val Val Phe Asp Ala Lys Gly Val Glu Phe Cys Asp Ala Met Pro
                485                 490                 495

Pro Gly Gln Ser Gly Phe Thr Asp Arg Asn Gly Val Arg Ser Pro His
                500                 505                 510

Tyr Glu Asp Gln Leu Lys Leu Tyr Glu Asn Phe Glu Cys Lys Thr Met
            515                 520                 525

Asp Val Thr His Ala Asp Ile Arg Arg Asn Ala Gln Ser Ser Thr Met
        530                 535                 540

Leu Leu Ile Gln Pro Gln Pro
545                 550
```

(2) INFORMATION FOR SEQ ID NO:33:

(i) SEQUENCE CHARACTERISTICS:
        (A) LENGTH: 557 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Ser Asn Met Trp Val Ile Gly Lys Ser Lys Ala Gln Asp Ala Lys Ala

-continued

```
1               5                   10                  15
Ile Met Val Asn Gly Pro Gln Phe Gly Trp Tyr Ala Pro Ala Tyr Thr
                20                  25                  30
Tyr Gly Ile Gly Leu His Gly Ala Gly Tyr Asp Val Thr Gly Asn Thr
                35                  40                  45
Pro Phe Ala Tyr Pro Gly Leu Gly Phe Gly His Asn Gly Val Ile Ser
                50                  55                  60
Trp Gly Ser Thr Ala Gly Phe Gly Asp Asp Val Asp Ile Phe Ala Glu
65                  70                  75                  80
Arg Leu Ser Ala Glu Lys Pro Gly Tyr Tyr Leu His Asn Gly Lys Trp
                85                  90                  95
Val Lys Met Leu Ser Arg Glu Glu Thr Ile Thr Val Lys Asn Gly Gln
                100                 105                 110
Ala Glu Thr Phe Thr Val Trp Arg Thr Val His Gly Asn Ile Leu Gln
                115                 120                 125
Thr Asp Gln Thr Thr Gln Thr Ala Tyr Ala Lys Ser Arg Ala Trp Asp
                130                 135                 140
Gly Lys Glu Val Ala Ser Leu Leu Ala Trp Thr His Gln Met Lys Ala
145                 150                 155                 160
Lys Asn Trp Gln Glu Trp Thr Gln Gln Ala Ala Lys Gln Ala Leu Thr
                165                 170                 175
Ile Asn Trp Tyr Tyr Ala Asp Val Asn Gly Asn Ile Gly Tyr Val His
                180                 185                 190
Thr Gly Ala Tyr Pro Asp Arg Gln Ser Gly His Asp Pro Arg Leu Pro
                195                 200                 205
Val Pro Gly Thr Gly Lys Trp Asp Trp Lys Gly Leu Leu Pro Phe Glu
                210                 215                 220
Met Asn Pro Lys Val Tyr Asn Pro Gln Ser Gly Tyr Ile Ala Asn Trp
225                 230                 235                 240
Asn Asn Ser Pro Gln Lys Asp Tyr Pro Ala Ser Asp Leu Phe Ala Phe
                245                 250                 255
Leu Trp Gly Gly Ala Asp Arg Val Thr Glu Ile Asp Arg Leu Leu Glu
                260                 265                 270
Gln Lys Pro Arg Leu Thr Ala Asp Gln Ala Trp Asp Val Ile Arg Gln
                275                 280                 285
Thr Ser Arg Gln Asp Leu Asn Leu Arg Leu Phe Leu Pro Thr Leu Gln
                290                 295                 300
Ala Ala Thr Ser Gly Leu Thr Gln Ser Pro Pro Arg Arg Gln Leu Val
305                 310                 315                 320
Glu Thr Leu Thr Arg Trp Asp Gly Ile Asn Leu Leu Asn Asp Asp Gly
                325                 330                 335
Lys Thr Trp Gln Gln Pro Gly Ser Ala Ile Leu Asn Val Trp Leu Thr
                340                 345                 350
Ser Met Leu Lys Arg Thr Val Val Ala Ala Val Pro Met Pro Phe Asp
                355                 360                 365
Lys Trp Tyr Ser Ala Ser Gly Tyr Glu Thr Thr Gln Asp Gly Pro Thr
                370                 375                 380
Gly Ser Leu Asn Ile Ser Val Gly Ala Lys Ile Leu Tyr Glu Ala Val
385                 390                 395                 400
Gln Gly Asp Lys Ser Pro Ile Pro Gln Ala Val Asp Leu Phe Ala Gly
                405                 410                 415
Lys Pro Gln Gln Glu Val Val Leu Ala Ala Leu Glu Asp Thr Trp Glu
                420                 425                 430
```

```
Thr Leu Ser Lys Arg Tyr Gly Asn Asn Val Ser Asn Trp Lys Thr Pro
            435                 440                 445

Ala Met Ala Leu Thr Phe Arg Ala Asn Asn Phe Phe Gly Val Pro Gln
450                 455                 460

Ala Ala Ala Glu Glu Thr Arg His Gln Ala Glu Tyr Gln Asn Arg Gly
465                 470                 475                 480

Thr Glu Asn Asp Met Ile Val Phe Ser Pro Thr Thr Ser Asp Arg Pro
                485                 490                 495

Val Leu Ala Trp Asp Val Val Ala Pro Gly Gln Ser Gly Phe Ile Ala
            500                 505                 510

Pro Asp Gly Thr Val Asp Lys His Tyr Glu Asp Gln Leu Lys Met Tyr
            515                 520                 525

Glu Asn Phe Gly Arg Lys Ser Leu Trp Leu Thr Lys Gln Asp Val Glu
530                 535                 540

Ala His Lys Glu Ser Gln Glu Val Leu His Val Gln Arg
545                 550                 555

(2) INFORMATION FOR SEQ ID NO:34:

(i) SEQUENCE CHARACTERISTICS:
        (A) LENGTH: 555 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Ser Asn Met Trp Val Ile Gly Lys Asn Lys Ala Gln Asp Ala Lys Ala
1               5                   10                  15

Ile Met Val Asn Gly Pro Gln Phe Gly Trp Tyr Ala Pro Ala Tyr Thr
                20                  25                  30

Tyr Gly Ile Gly Leu His Gly Ala Gly Tyr Asp Val Thr Gly Asn Thr
            35                  40                  45

Pro Phe Ala Tyr Pro Gly Leu Val Phe Gly His Asn Gly Thr Ile Ser
    50                  55                  60

Trp Gly Ser Thr Ala Gly Phe Gly Asp Asp Val Asp Ile Phe Ala Glu
65              70                  75                  80

Lys Leu Ser Ala Glu Lys Pro Gly Tyr Tyr Gln His Asn Gly Glu Trp
                85                  90                  95

Val Lys Met Leu Ser Arg Lys Glu Thr Ile Ala Val Lys Asp Gly Gln
                100                 105                 110

Pro Glu Thr Phe Thr Val Trp Arg Thr Leu Asp Gly Asn Val Ile Lys
            115                 120                 125

Thr Asp Thr Arg Thr Gln Thr Ala Tyr Ala Lys Ala Arg Ala Trp Ala
130                 135                 140

Gly Lys Glu Val Ala Ala Leu Leu Ala Trp Thr His Gln Met Lys Ala
145                 150                 155                 160

Lys Asn Trp Pro Glu Trp Thr Gln Gln Ala Ala Lys Gln Ala Leu Thr
                165                 170                 175

Ile Asn Trp Tyr Tyr Ala Asp Val Asn Gly Asn Ile Gly Tyr Val His
            180                 185                 190

Thr Gly Ala Tyr Pro Asp Arg Gln Pro Gly His Asp Pro Arg Leu Pro
        195                 200                 205

Val Pro Asp Gly Lys Trp Asp Trp Lys Gly Leu Leu Ser Phe Asp Leu
210                 215                 220
```

```
Asn Pro Lys Val Tyr Asn Pro Gln Ser Gly Tyr Ile Ala Asn Trp Asn
225                 230                 235                 240

Asn Ser Pro Gln Lys Asp Tyr Pro Ala Ser Asp Leu Phe Ala Phe Leu
            245                 250                 255

Trp Gly Gly Ala Asp Arg Val Thr Glu Ile Asp Thr Ile Leu Asp Lys
        260                 265                 270

Gln Pro Arg Phe Thr Ala Asp Gln Ala Trp Asp Val Ile Arg Gln Thr
    275                 280                 285

Ser Leu Arg Asp Leu Leu Arg Leu Phe Leu Pro Ala Leu Lys Asp Ala
290                 295                 300

Thr Ala Asn Leu Ala Glu Asn Asp Pro Arg Arg Gln Leu Val Asp Lys
305                 310                 315                 320

Leu Ala Ser Trp Asp Gly Glu Asn Leu Val Asn Asp Asp Gly Lys Thr
                325                 330                 335

Tyr Gln Gln Pro Gly Ser Ala Ile Leu Asn Ala Trp Leu Thr Ser Met
            340                 345                 350

Leu Lys Arg Thr Leu Val Ala Ala Val Pro Ala Pro Phe Gly Lys Trp
        355                 360                 365

Tyr Ser Ala Ser Gly Tyr Glu Thr Thr Gln Asp Gly Pro Thr Gly Ser
    370                 375                 380

Leu Asn Ile Ser Val Gly Ala Lys Ile Leu Tyr Glu Ala Leu Gln Gly
385                 390                 395                 400

Asp Lys Ser Pro Ile Pro Gln Ala Val Asp Leu Phe Gly Gly Lys Pro
                405                 410                 415

Glu Gln Glu Val Ile Leu Ala Ala Leu Asp Asp Ala Trp Gln Thr Leu
            420                 425                 430

Ser Lys Arg Tyr Gly Asn Asp Val Thr Gly Trp Lys Thr Pro Ala Met
        435                 440                 445

Ala Leu Thr Phe Arg Ala Asn Asn Phe Phe Gly Val Pro Gln Ala Ala
    450                 455                 460

Ala Lys Glu Ala Arg His Gln Ala Glu Tyr Gln Asn Arg Gly Thr Glu
465                 470                 475                 480

Asn Asp Met Ile Val Phe Ser Pro Thr Ser Gly Asn Arg Pro Val Leu
                485                 490                 495

Ala Trp Asp Val Val Ala Pro Gly Gln Ser Gly Phe Ile Ala Pro Asp
            500                 505                 510

Gly Lys Ala Asp Lys His Tyr Asp Asp Gln Leu Lys Met Tyr Glu Ser
        515                 520                 525

Phe Gly Arg Lys Ser Leu Trp Leu Thr Pro Gln Asp Val Asp Glu His
    530                 535                 540

Lys Glu Ser Gln Glu Val Leu Gln Val Gln Arg
545                 550                 555

(2) INFORMATION FOR SEQ ID NO:35:

(i) SEQUENCE CHARACTERISTICS:
        (A) LENGTH: 528 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Ser Asn Ala Ala Ile Val Gly Ser Glu Lys Ser Ala Thr Gly Asn Ala
1               5                   10                  15
```

```
Leu Leu Phe Ser Gly Pro Gln Val Gly Phe Val Ala Pro Gly Phe Leu
            20                  25                  30

Tyr Glu Val Gly Leu His Ala Pro Gly Phe Asp Met Glu Gly Ser Gly
            35                  40                  45

Phe Ile Gly Tyr Pro Phe Ile Met Phe Gly Ala Asn Asn His Phe Ala
        50                  55                  60

Leu Ser Ala Thr Ala Gly Tyr Gly Asn Val Thr Asp Ile Phe Glu Glu
65                      70                  75                  80

Lys Leu Asn Thr Lys Asn Ser Ser Gln Tyr Leu Tyr Lys Gly Lys Trp
                85                  90                  95

Arg Asp Met Glu Lys Arg Lys Glu Ser Phe Thr Val Lys Gly Asp Asn
                100                 105                 110

Gly Glu Lys Lys Thr Val Glu Lys Ile Tyr Tyr Arg Thr Val His Gly
            115                 120                 125

Pro Val Ile Ser Arg Asp Glu Thr Asn Lys Val Ala Tyr Ser Lys Tyr
            130                 135                 140

Val Ser Phe Arg Gly Thr Glu Glu Ala Gln Ser Met Ser Ala Tyr Met
145                 150                 155                 160

Lys Ala Asn Trp Ala Lys Asn Leu Lys Glu Phe Glu Asn Ala Ala Ser
                165                 170                 175

Glu Tyr Thr Met Ser Leu Asn Trp Tyr Tyr Ala Asp Lys Lys Gly Asp
            180                 185                 190

Ile Ala Tyr Tyr His Val Gly Arg Tyr Pro Val Arg Asn Asn Lys Ile
            195                 200                 205

Asp Glu Arg Ile Pro Thr Pro Gly Thr Gly Glu Tyr Glu Trp Lys Gly
210                 215                 220

Phe Ile Pro Phe Lys Glu Asn Pro His Val Ile Asn Pro Lys Asn Gly
225                 230                 235                 240

Tyr Val Val Asn Trp Asn Asn Lys Pro Ser Lys Glu Trp Val Asn Gly
                245                 250                 255

Glu Tyr Ser Tyr Tyr Trp Gly Glu Asp Asn Arg Val Gln Gln Tyr Ile
            260                 265                 270

Asn Gly Gly Met Glu Ala Arg Gly Lys Val Thr Leu Glu Asp Ile Asn
            275                 280                 285

Glu Ile Asn Tyr Thr Ala Ser Phe Ala Gln Leu Arg Ala Asn Leu Phe
290                 295                 300

Lys Pro Leu Leu Ile Asp Val Leu Asp Lys Asn Lys Ser Thr Asn Gly
305                 310                 315                 320

Asn Tyr Thr Tyr Leu Ile Glu Lys Leu Glu Glu Trp Asn Asn Leu Lys
                325                 330                 335

Glu Asp Glu Asn Lys Asp Gly Tyr Tyr Asp Ala Gly Ile Ala Ala Phe
                340                 345                 350

Phe Asp Glu Trp Trp Asn Asn Leu His Asp Lys Leu Phe Met Asp Glu
            355                 360                 365

Leu Gly Asp Phe Tyr Gly Ile Thr Lys Glu Ile Thr Asp His Arg Tyr
            370                 375                 380

Gly Ala Ser Leu Ala Tyr Lys Asn Ile Ser Lys Glu Ser Thr Asn Tyr
385                 390                 395                 400

Lys Trp Val Lys Trp Val Asn Val Asp Gln Glu Lys Ile Ile Met Glu
                405                 410                 415

Ser Thr Asn Glu Val Leu Ala Lys Leu Gln Ser Glu Lys Gly Leu Lys
            420                 425                 430
```

```
Ala Glu Lys Trp Arg Met Pro Ile Lys Thr Met Thr Phe Gly Glu Lys
        435                 440                 445

Ser Leu Ile Gly Ile Pro His Gly Tyr Gly Ser Met Thr Pro Ile Ile
        450                 455                 460

Glu Met Asn Arg Gly Ser Glu Asn His Tyr Ile Glu Met Thr Pro Lys
465                 470                 475                 480

Gly Pro Ser Gly Phe Asn Ile Thr Pro Pro Gly Gln Ile Gly Phe Val
                485                 490                 495

Lys Lys Asp Gly Thr Ile Ser Asp His Tyr Asp Asp Gln Leu Val Met
                500                 505                 510

Phe Ala Glu Trp Lys Phe Lys Pro Tyr Leu Phe Asn Lys Lys Asp Ile
        515                 520                 525

(2) INFORMATION FOR SEQ ID NO:36:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

Ser Asn Val Trp Leu Val Gly Lys Thr Lys Ala Ser Gly Ala Lys Ala
1               5                   10                  15

Ile Leu Leu Asn Gly Pro Gln Phe Gly Trp Phe Asn Pro Ala Tyr Thr
                20                  25                  30

Tyr Gly Ile Gly Leu His Gly Ala Gly Phe Asn Ile Val Gly Asn Thr
            35                  40                  45

Pro Phe Ala Tyr Pro Ala Ile Leu Phe Gly His Asn Gly His Val Ser
50                  55                  60

Trp Gly Ser Thr Ala Gly Phe Gly Asp Gly Val Asp Ile Phe Ala Glu
65                  70                  75                  80

Gln Val Ser Pro Glu Asp Pro Asn Ser Tyr Leu His Gln Gly Gln Trp
                85                  90                  95

Lys Lys Met Leu Ser Arg Gln Glu Thr Leu Asn Val Lys Gly Glu Gln
                100                 105                 110

Pro Ile Thr Phe Glu Ile Tyr Arg Thr Val His Gly Asn Val Val Lys
            115                 120                 125

Arg Asp Lys Thr Thr His Thr Ala Tyr Ser Lys Ala Arg Ala Trp Asp
            130                 135                 140

Gly Lys Glu Leu Thr Ser Leu Met Ala Trp Val Lys Gln Gly Gln Ala
145                 150                 155                 160

Gln Asn Trp Gln Gln Trp Leu Asp Gln Ala Gln Asn Gln Ala Leu Thr
                165                 170                 175

Ile Asn Trp Tyr Tyr Ala Asp Lys Asp Gly Asn Ile Gly Tyr Val His
            180                 185                 190

Thr Gly His Tyr Pro Asp Arg Gln Ile Asn His Asp Pro Arg Leu Pro
            195                 200                 205

Val Ser Gly Thr Gly Glu Trp Asp Trp Lys Gly Ile Gln Pro Phe Ala
210                 215                 220

Asn Asn Pro Lys Val Tyr Asn Pro Lys Ser Gly Tyr Ile Ala Asn Trp
225                 230                 235                 240

Asn Asn Ser Pro Ala Lys Asn Tyr Pro Ala Ser Asp Leu Phe Ala Phe
            245                 250                 255
```

-continued

```
Leu Trp Gly Ser Ala Asp Arg Val Lys Glu Ile Asp Asn Arg Ile Glu
            260                 265                 270

Ala Tyr Asp Lys Leu Thr Ala Asp Asp Met Trp Ala Ile Leu Gln Gln
            275                 280                 285

Thr Ser Arg Val Asp Leu Asn His Arg Leu Phe Thr Pro Phe Leu Thr
        290                 295                 300

Gln Ala Thr Gln Gly Leu Pro Ser Asn Asp Asn Ser Val Lys Leu Val
305                     310                 315                 320

Ser Met Leu Gln Gln Trp Asp Gly Ile Asn Gln Leu Ser Ser Asp Gly
                325                 330                 335

Lys His Tyr Ile His Pro Gly Ser Ala Tyr Leu Asp Ile Trp Leu Lys
            340                 345                 350

Glu Met Leu Lys Ala Thr Leu Gly Gln Thr Val Pro Ala Pro Phe Asp
            355                 360                 365

Lys Trp Tyr Leu Ala Ser Gly Tyr Glu Thr Thr Gln Glu Gly Pro Thr
            370                 375                 380

Gly Ser Leu Asn Ile Ser Thr Gly Ala Lys Leu Leu Tyr Glu Ser Leu
385                     390                 395                 400

Leu Glu Asp Lys Ser Pro Ile Ser Gln Ser Ile Asp Leu Phe Ser Gly
                405                 410                 415

Gln Pro Gln Asn Asp Val Ile Arg Lys Thr Leu Asn Thr Thr Tyr Gln
                420                 425                 430

Lys Met Ile Glu Lys Tyr Gly Asp Asn Pro Ala Asn Trp Gln Thr Pro
            435                 440                 445

Ala Thr Ala Leu Thr Phe Arg Glu Asn Asn Phe Phe Gly Ile Pro Gln
            450                 455                 460

Ala Leu Pro Gln Glu Asn Phe His Gln Asn Glu Tyr His Asn Arg Gly
465                 470                 475                 480

Thr Glu Asn Asp Leu Ile Val Phe Thr Glu Glu Gly Val Ser Ala Trp
                485                 490                 495

Asp Val Val Ala Pro Gly Gln Ser Gly Phe Ile Ser Pro Gln Gly Lys
                500                 505                 510

Pro Ser Pro His Tyr Gln Asp Gln Leu Ser Leu Tyr Gln Gln Phe Gly
            515                 520                 525

Lys Lys Pro Leu Trp Leu Asn Ser Glu Asp Val Ala Pro Tyr Ile Glu
        530                 535                 540

Ser Thr Glu Thr Leu Ile Ile Glu Arg
545                 550
```